US011169082B2

(12) United States Patent
Mukhtar

(10) Patent No.: US 11,169,082 B2
(45) Date of Patent: Nov. 9, 2021

(54) UNIVERSAL DEBONDING TEST APPARATUS FOR CARBON FIBER REINFORCED POLYMER-CONCRETE SYSTEM AND METHOD FOR SEQUENTIAL MULTI-TESTING

(71) Applicant: King Fahd University of Petroleum and Minerals, Dhahran (SA)

(72) Inventor: Faisal M. Mukhtar, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 138 days.

(21) Appl. No.: 16/530,543

(22) Filed: Aug. 2, 2019

(65) Prior Publication Data

US 2021/0033522 A1   Feb. 4, 2021

(51) Int. Cl.
| | | |
|---|---|---|
| G01N 19/04 | (2006.01) | |
| G01N 3/24 | (2006.01) | |
| G01N 3/04 | (2006.01) | |
| G01N 33/24 | (2006.01) | |
| G01N 33/00 | (2006.01) | |

(52) U.S. Cl.
CPC .............. *G01N 19/04* (2013.01); *G01N 3/04* (2013.01); *G01N 3/24* (2013.01); *G01N 33/24* (2013.01); *G01N 2033/0003* (2013.01); *G01N 2203/0023* (2013.01); *G01N 2203/0025* (2013.01); *G01N 2203/0091* (2013.01); *G01N 2203/0252* (2013.01); *G01N 2203/0423* (2013.01)

(58) Field of Classification Search
CPC ............ G01N 19/04; G01N 3/24; G01N 3/04; G01N 33/24; G01N 2203/0003; G01N 2203/0023; G01N 2203/0091; G01N 2203/0252; G01N 2203/0423; G01N 2203/0025

See application file for complete search history.

(56) References Cited

U.S. PATENT DOCUMENTS 5,739,436 A   4/1998   Trautwein

FOREIGN PATENT DOCUMENTS

| CN | 104344989 A | 2/2015 |
| CN | 205593860 U | 9/2016 |
| CN | 107247001 A | 10/2017 |
| CN | 107817172 A | 3/2018 |

*Primary Examiner* — Jonathan M Dunlap
(74) *Attorney, Agent, or Firm* — Oblon, McClelland, Maier & Neustadt, L.L.P.

(57) ABSTRACT

A test apparatus used for simulating debonding between a carbon fiber reinforced polymer (CFRP) and concrete in a CFRP-strengthened structure consists of a primary structural block, a secondary structural block, an adjustable hanger, a receiving slot, an attachment mechanism, a pull-off disk, a connecting plate having a plurality of rods. The adjustable hanger and the secondary structural block are slidably positioned into the receiving slot that traverses into a structural body of the primary structural block. The adjustable hanger is mainly used during double-shearing tests and mixed-mode tests, wherein both shearing and peeling is analyzed in mixed-mode tests. The secondary structural block is used in double-shear tests, mixed-mode tests, single-shear tests, tension pull-off tests, and beam-bend tests. The attachment mechanism, which holds the primary structural block, the secondary structural block, and the adjustable hanger together, is also used during single-shear tests and beam-bend tests.

19 Claims, 18 Drawing Sheets

UNIVERSAL DEBONDING TEST APPARATUS FOR CARBON FIBER REINFORCED POLYMER-CONCRETE SYSTEM AND METHOD FOR SEQUENTIAL MULTI-TESTING

BACKGROUND

Field of the Invention

The present disclosure relates to an evaluation and testing method, apparatus and system for interfacial bonds, such as between an externally bonded carbon fiber reinforced polymer (CFRP) and a concrete structure. In particular, the present disclosure describes a universal test apparatus and system that improves the traditional double-shear test method and other major CFRP-concrete tests such as the single-shear test, mixed-mode test, the tension pull-off test, and the beam-bending test.

Description of the Related Art

Carbon fiber reinforced polymer (CFRP) sheets are used when an existing concrete structure needs to be strengthened or repaired through retrofitting. Being lightweight, corrosion free, and having improved thermal characteristics are some notable reasons for using CFRP over other alternatives such as steel plates. The overall performance of a CFRP-strengthened structure mainly depends on the CFRP-concrete bond and the performance of the CFRP-concrete bond. However, environmental conditions such as high temperatures, humidity, and corrosion environments can also affect the performance of a CFRP-strengthened structure.

Bond stress characteristics play a major role in the behavior of externally bonded reinforcement/CFRP-strengthened reinforced concrete beams. The bond characteristics are normally determined via experimental data obtained from small-scale bond tests. However, the research community is yet to agree on a unified experimental set-up and testing procedure for these tests. The lack of standard tests leads to high variability in published results and hinders the development of reliable design models. Moreover, temperature and moisture are two dominant conditions that have significant impacts on a variety of mechanical and durability issues. Exposure to high temperature and humidity can result in adhesive bond degradation which causes a rapid decrease in efficiency of the entire strengthened system. In one instance, a recorded ambient temperature, to which an adhesive layer between CFRP and concrete is subjected to, reached 65-Centigrade (° C.), which was 20° C. higher than the glass transition temperature of typical commercially available adhesives based on epoxy resin. Thus, accurate prior testing for CFRP-concrete bonds in CFRP-strengthened structures is essential since the quality of the interfacial bond ensures satisfactory performance of the CFRP/FRP-strengthened structure.

Premature debonding of a CFRP-concrete interface undermines the capacity of a CFRP-strengthened structure. In some instances, the CFRP-concrete can debond even when only 30% of the capacity of the CFRP-strengthened structure is in use. To seek optimal performance from a CFRP-strengthened structure, laboratory set ups, field methods, or a combination of both laboratory set ups and field methods are used to analyze the CFRP-concrete debonding characteristics. The controlled conditions provided within a laboratory environment are vital to simulate different loading scenarios that occur in practical use.

Conventional tests for CFRP-concrete bonds are based on the manner and/or mode of stress transfer between the CFRP and the concrete. Five major test types are executed to analyze manner and/or mode of stress transfer, wherein each of the test types have unique characteristics, attributes, powers, and limitations. Namely, the five test types are single-shear test, double-shear test, mixed-mode shear test, beam-bending test, and tension pull-off test. Since each of the tests have unique characteristics, a test type used for testing one scenario may not be suitable for testing a different scenario. Testing standards that can be, but is not limited to, ASTM D7522/D7522M, ASTM D7958/D7958M, ASTM D7913/D7913M, and ACI 440.3R-12 are incorporated herein by reference in its entirety.

As an example, multiple sources for pull-off test recommendations or standards have been published including the International Concrete Repair Institute (ICRI) Guideline No. 03739 (2004), the Army Corps of Engineers Technical Report REMR-CS-61 (1999), ACI 503R (1993), and ASTM D7522 (2009). ICRI recommends core drilling a minimum depth of 25 mm (1") into the existing substrate, while ASTM D7522 requires core drilling between 6 mm (0.25") and 12 mm (0.5") into the substrate. ACI 503R recommends "core drill through the coating and down barely into the subsurface."

As shown in FIG. 1, to perform a single-shear test, one end of a CFRP sheet is initially fixed to a concrete prism through adhesive such that an opposite end of the CFRP sheet extends outwards from the concrete prism. In other words, a suitable length of the CFRP sheet is left detached from the concrete prism as a free end for load application. When single-shear testing is performed, a first clamping system is used to hold the concrete prism and a second clamping system is used to hold the detached portion/free end of the CFRP sheet. A load is applied at the free end of the CFRP sheet until bond failure. By applying a load at the free end of the CFRP sheet, the CFRP-concrete interface is subjected to a pure shear referred to as a mode-I loading pattern. A challenge related to the discussed single-shear test is the difficulty in securing the CFRP sheet with the clamping system so that a load can be applied at the free end of the CFRP sheet. Another challenge with the discussed single-shear test is the need to focus on secondary peeling effects. The secondary peeling effects generally depend on the sample size of the CFRP sheet and can occur due to the stresses applied during the single-shear test. With the existing testing method, a slight error in alignment can cause eccentricity in the CFRP sheet resulting in decreased accuracy of results.

A double-shear test, shown in FIG. 3, is commonly used to address the issues related to existing single-shear test methods. The double-shear test is known to be the simplest debonding test method since only an axial loading machine is required. In contrast to the single-shear test described earlier, in the double-shear test a holding mechanism is not required to hold the concrete prism and the CFRP sheet/strip that is tested. In general, when the double-shear test is executed, two similarly sized concrete blocks are linearly aligned to each other. Typically, the dimensions of each of the concrete blocks are similar to the dimensions of the concrete block used in the single-shear test. The two concrete blocks are linearly aligned such that the top surfaces of the concrete blocks are facing each other. A steel rod/loading rebar is partially embedded into a bottom surface of each of the concrete blocks. Thus, when the top surfaces of the two concrete blocks are facing each other, the steel rods embedded into the bottom surfaces extend outwards in opposite directions. To perform the double-shear test, two CFRP strips are adhered to opposite surfaces of the two-concrete blocks. After epoxy curing of the two CFRP strips, axial loading is applied through each of the steel rods in a laboratory environment to test the failure of the bond between each of the two CFRP strips and each of the two concrete blocks. The inconvenience in handling heavy concrete blocks is one disadvantage related to the existing double-shear testing method. In particular, maintaining the linear arrangement between the concrete blocks can be challenging during a testing process. The uneven load distribution between the two CFRP strips and the instability following the debonding of a CFRP strip-concrete bond are among some of the other disadvantages of the existing double-shear testing method. The debonding results from the double-shear test are also dependent on where the debonding is initiated. Additionally, maintaining eccentricity in loading can be challenging with the existing double-shear testing method.

Generally, in order to address the issues listed above and as an alternative to the discussed double-shear testing method, a U-shaped CFRP piece is attached to one concrete block instead of two. With this approach, some of the previously discussed issues related to handling are resolved. However, the need to find a proper clamping mechanism to hold the U-shaped CFRP piece can be inconvenient. Additionally, other issues such as eccentricity, the inability to perform mixed-mode tests for shearing and peeling, and the inability to eliminate uneven load distribution are some of the drawbacks possible when an improperly designed clamping mechanism is used with a U-shaped CFRP piece for double-shear testing.

A beam-bending type test has the advantage of simulating, to some extent, the debonding failure in structural beams. In order to conduct the beam-bending type test, a crack path is defined on a concrete specimen. A first way of defining a crack path is to cast a monolithic beam of a suitable size with a crack facing downwards along a center of the beam. A second way of defining a crack path is to cast a beam with two halves and join them using a hinge at the top as seen in FIG. 4. Thus, a gap between the two halves can serve as a predefined crack during loading. The CFRP sheet is applied at a bottom end of the beam opposite the hinge. When curing the epoxy is complete, a four-point loading test is carried out till failure of the bond between the CFRP sheet and the concrete. Even though the beam-bending type test addresses certain concomitant compressive stresses, the complete behavior of a real CFRP-strengthened beam is not simulated with the existing beam-bending type tests. For example, the peeling effects are not addressed by the existing beam-bending type tests.

Similar to the single-shear test and the double-shear test, the beam-bending test is also mainly mode-I since debonding occur through shearing. Therefore, a different mixed-mode testing method is used if both shearing and peeling needs to be simulated. Even though multiple variations exist for the mixed-mode testing method, the common objective is to analyze the shear-peeling interface and a corresponding load. Depending on the peel-to-shear ratio required, the mixed-mode test can be conducted to simulate the performance of the CFRP-concrete bond under different predominant loading modes expected in a real structure. As further illustrated in FIG. 2, the single-shear test is generally modified for mixed-mode testing by applying the load on the free end of the CFRP strip at an angle. As further illustrated in FIG. 3, the double-shear test is generally modified for mixed-mode testing by using differently sized concrete blocks. However, with the approach of using differently sized concrete blocks, adjusting the test for varying shear-peel ratios is not permitted. Moreover, the approach of using differently sized concrete blocks is uneconomical and requires significant user interaction when handling the concrete blocks.

The tension pull-off test, shown in FIG. 5, is another CFRP-concrete bond test method. When executing the tension pull-off test, a circular core is engraved into a CFRP sheet that is mounted onto a concrete surface. A metal disk, also referred to as a dolly or tension pull-off disk, is adhered onto the circular core using epoxy. To do so, a size of the metal disk is selected to be equivalent to the size of the circular core or marginally smaller than the circular core. After epoxy curing, a direct force is used to pull out the dolly which applies a direct force on the CFRP-concrete bond. The load that causes debonding is used as an indication for the CFRP-concrete bond strength under direct tension. Even though the described method can be implemented in a laboratory or in the field, the drawback is that CFRP-concrete structures rarely undergo such direct pull forces in practice. Therefore, in order to get an accurate understanding of the CFRP-concrete bond strength, other previously listed testing methods need to be executed in conjunction with the tension pull-off test and the accuracy of results can be hindered. Moreover, specific conditions need to be satisfied when performing the tension pull-off test. As an example, Guideline No. 03739 by the International Concrete Repair Institute (ICRI) also targets pull-off tests as a way to evaluate the tensile strength of a concrete surface repair. The ICRI Technical Guideline No. 03739 (2004) recommends a minimum depth of core drill to be 1 in (25 mm) for a 2 in (50 mm) dolly. On the other hand, ASTM D7522 (2009) recommends for the same size dolly, a core depth of 0.25 in (6 mm) to 0.50 in (12 mm). Finally, ACI 503R (1993) advises to barely core drill into the substrate.

In general, the tests described above provide predictions with a large dispersion of results amongst them. Even though the equipment used in the listed testing methods are effective to some extent, the present inventor has recognized that the lack of a laboratory device/assembly that can adopt/adjust according to the test type is desirable. More specifically, each of the major test types as performed in the prior art requires different equipment and systems which are mostly purpose-built on an ad hoc basis. The lack of a device that can adopt according to the test type can lead to time consuming and challenging testing procedures.

Referring again to the prior art, for convenience purposes, testing methods that require less equipment are generally used. For example, the double-shear test is generally used as a common test method since only axial loading is required during the test. However, the results related to shearing from one double-shear test can vary from the results related to shearing obtained from a different testing method. Thus, results from other testing methods may still be preferred against the results of the improved double-shear test.

Accordingly it is one object of the present disclosure to provide a device/system that is based upon the double-shear test but is adaptable to all other test types such that consistent results can be obtained throughout all the test types and thereby eliminate the difficulties and inaccuracies associated with purpose built testing equipment.

SUMMARY OF THE INVENTION

In a first embodiment, the present disclosure describes a debonding test apparatus for analyzing and simulating interfacial bonds between carbon fiber reinforced polymer (CFRP) and concrete in CFRP-strengthened structures includes a primary structural block, a secondary structural block, an adjustable hanger, a receiving slot, and an attachment mechanism. The adjustable hanger, which is used during double-shear testing and shear-peeling testing, is slidably positioned through a body of the primary structural block. The adjustable hanger can also be used when studying the influence of a concrete specimen size during a double-shear test. The secondary structural block, which is used during double shear-testing, mixed-mode testing, single-shear testing, tension pull-off testing, and beam-bending testing, is also slidably positioned through the body of the primary structural block. The attachment mechanism, which can vary in different embodiments, holds the primary structural block, the secondary structural block, and the adjustable hanger together such that the adjustable hanger is positioned atop the secondary structural block within the receiving slot.

The debonding test apparatus further includes a tension pull-off disk, a connecting plate, and a plurality of rods extending from the connecting plate. The tension pull-off disk, which is connected to a threaded protrusion, is used to conduct the tension pull-off test, single-shear test, and an alternative double-shear test arrangement that minimizes eccentricity. The connecting plate and the plurality of rods are used during the beam-bending test, the single-shear test, and the double-shear test that minimizes eccentricity. In doing so, the connecting plate is attached to the secondary structural block using hinges coupled together with a bolt/nut/washer system. The plurality of rods is positioned into a set of receiving holes that is drilled into the concrete prism. When single-shear testing and double-shear testing that minimize eccentricity are performed, the tension pull-off disk is used to further secure the connecting plate to the secondary structural block to prevent relative movements. When the beam-bending test is conducted, the tension pull-off disk is not used since the debonding apparatus needs to rotate relative to the concrete prism. However, when the beam-bending test is conducted, the plurality of rods is secured with the concrete prism using a nut/bolt/washer system to prevent relative movements.

In another embodiment, the present disclosure describes a universal test apparatus that can be adjusted to test for double-shear testing, single-shear testing, mixed-mode testing, tension pull-off testing, and beam-bending testing.

In another embodiment, the device can be customized according to user needs and is not limited to conducting a specific CFRP-concrete bond test type.

In another embodiment, different CFRP-concrete test types can be carried out using the device by performing sequential multi-testing.

In a further embodiment, the apparatus is configured with a double mixed-mode test that includes adjustability to fit different concrete specimen sizes, alternative double-shear test arrangements that minimize eccentricity, and capability for minimizing specimen size by half compared to traditional double-shear test specimen.

In another embodiment, the present disclosure includes an apparatus configured for single-shear testing, tension pull-off testing, and beam-bending testing and thereby substitute purpose-built devices and/or systems.

In another embodiment, the present disclosure includes a method for performing different test types such as: a method of sequentially conducting tests (multi-testing) on a single concrete specimen with the use of a fixed-position loading machine to obtain a preferred set of results economically and efficiently.

The present disclosure describes an apparatus that has a more versatile and improved double-shear testing capability. In embodiments, the apparatus of the present disclosure addresses problems and limitations pertinent to conventional double-shear test methods by providing mixed-mode loading patterns and a ratio between shearing and peeling to be adjusted during testing. In contrast to conventional testing methods, the test apparatus and method of the present disclosure can be used with concrete specimens of varying sizes. The adjustability of the apparatus allows a user to minimize eccentricity and other comparable drawbacks related to conventional testing methods. The present disclosure describes how the apparatus can be used for conducting all debonding test types sequentially. Since the same apparatus is used for all test types, the overall accuracy of the results is improved.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

All illustrations of the drawings are for the purpose of describing selected versions of the present disclosure and are not intended to limit the scope of the present disclosure.

The present disclosure describes a debonding test apparatus that can be used for analyzing interfacial bonds between carbon fiber reinforced polymer (CFRP) and concrete. By utilizing the test apparatus described, the stress transfer of a CFRP-strengthened structure can be simulated and evaluated.

Different testing setups and methods are available to investigate the bond behavior and debonding failures of surface bonded CFRP sheets. The testing configurations can be classified into four categories on the basis of the type of stresses generated in concrete: I) tension; II) direct or pure shear; III) combined shear and tension; and IV) flexure. The results of numerical and experimental studies indicate that testing configurations affect test results. Furthermore, it has also been reported that small variations in test setups within a selected method, such as the height of the support block, may also have significant effects on the bond behavior. Considering these factors, the need for a unified experimental set-up is clearly seen.

Figure 1:
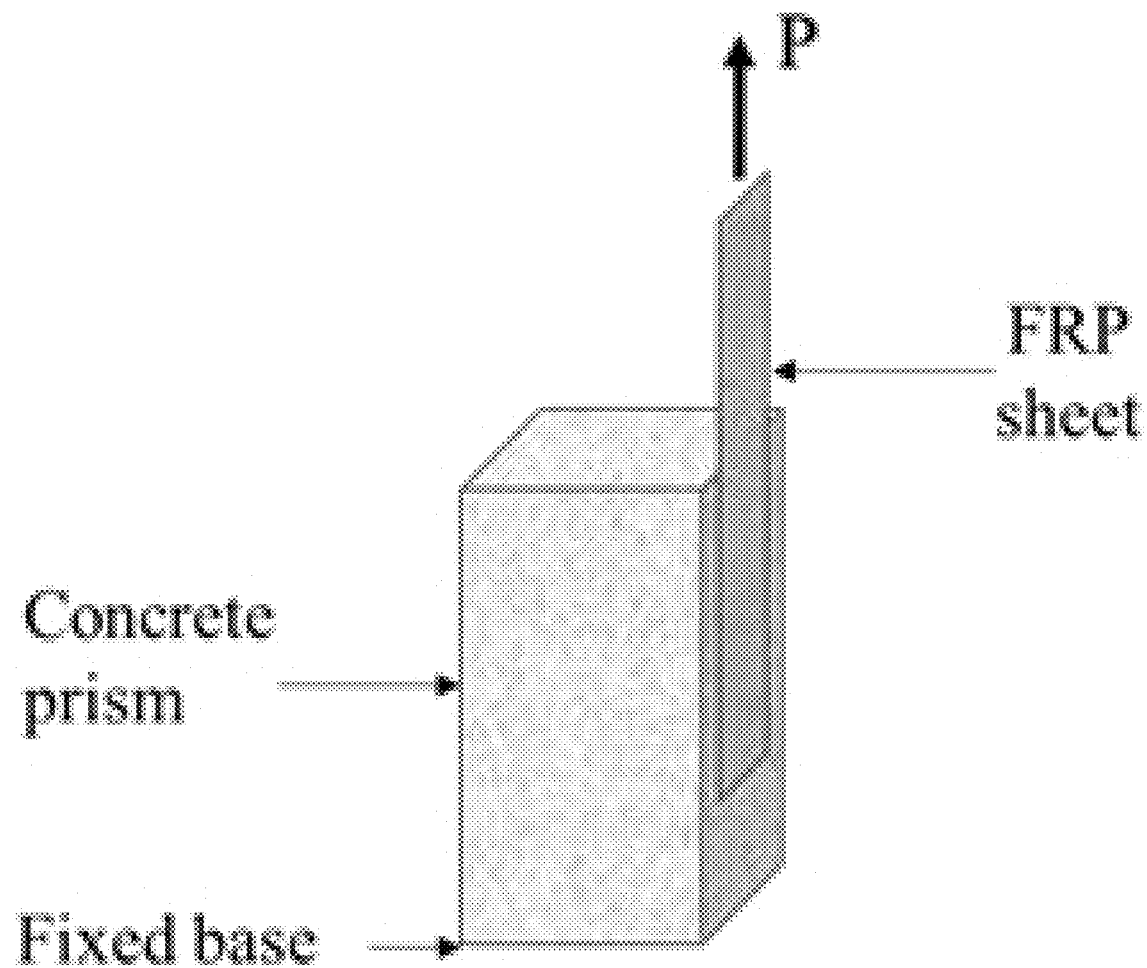
FIG. 1 is an illustration of an existing single-shear testing method.
Figure 2:
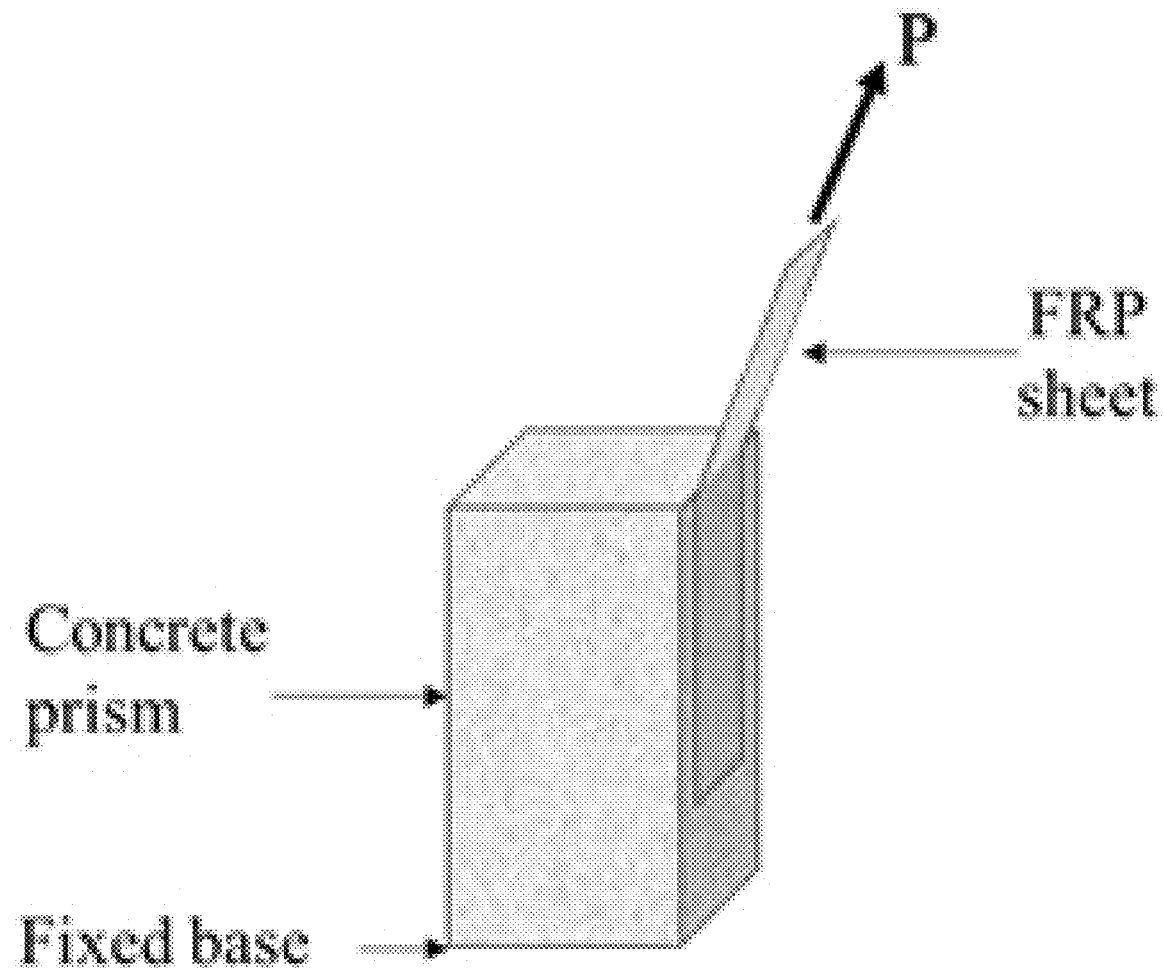
FIG. 2 is an illustration of an existing mixed-mode testing method, based on a modified form of the single-shear test, used to analyze shearing and peeling.
Figure 3:
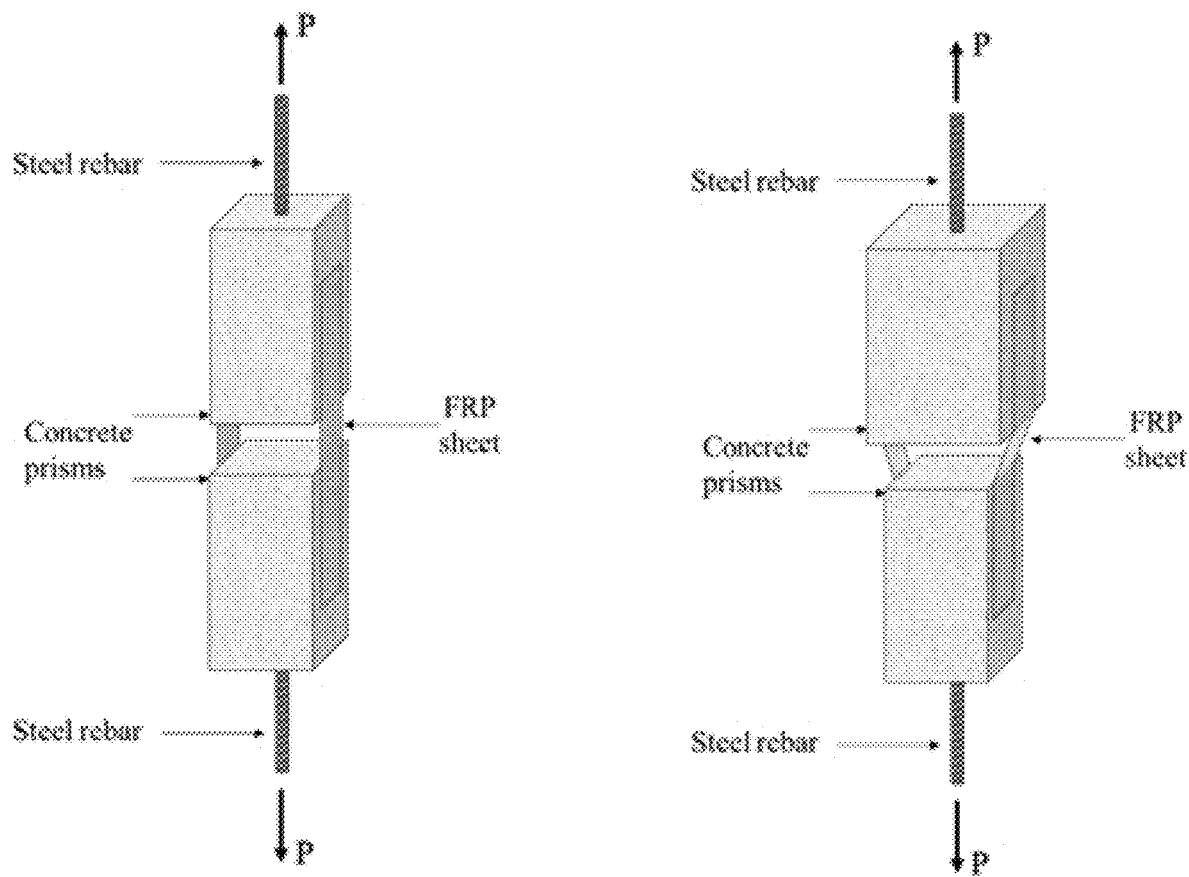
FIG. 3 is an illustration of an existing double-shear testing method and an illustration of another mixed-mode testing method used to analyze shearing and peeling with differently sized concrete specimens.
Figure 4:
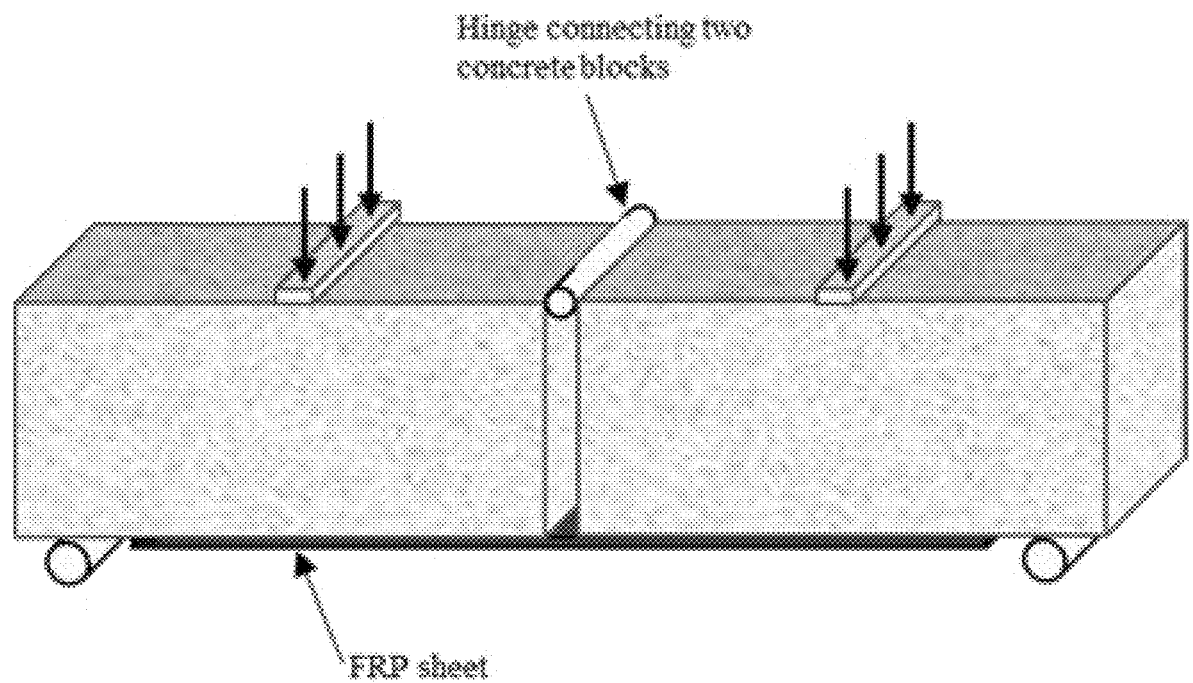
FIG. 4 is an illustration of an existing method used to analyze beam-bending properties of a CFRP-strengthened structure.
Figure 5:
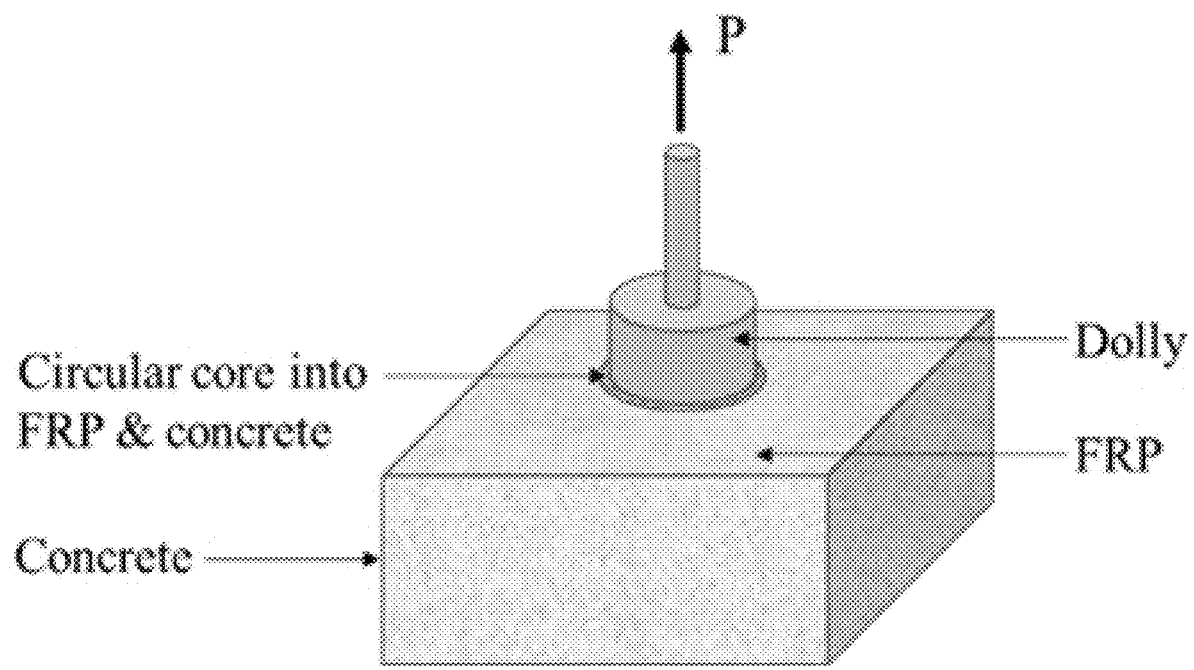
FIG. 5 is an illustration of an existing method used for tension pull-off testing.
Figure 6:
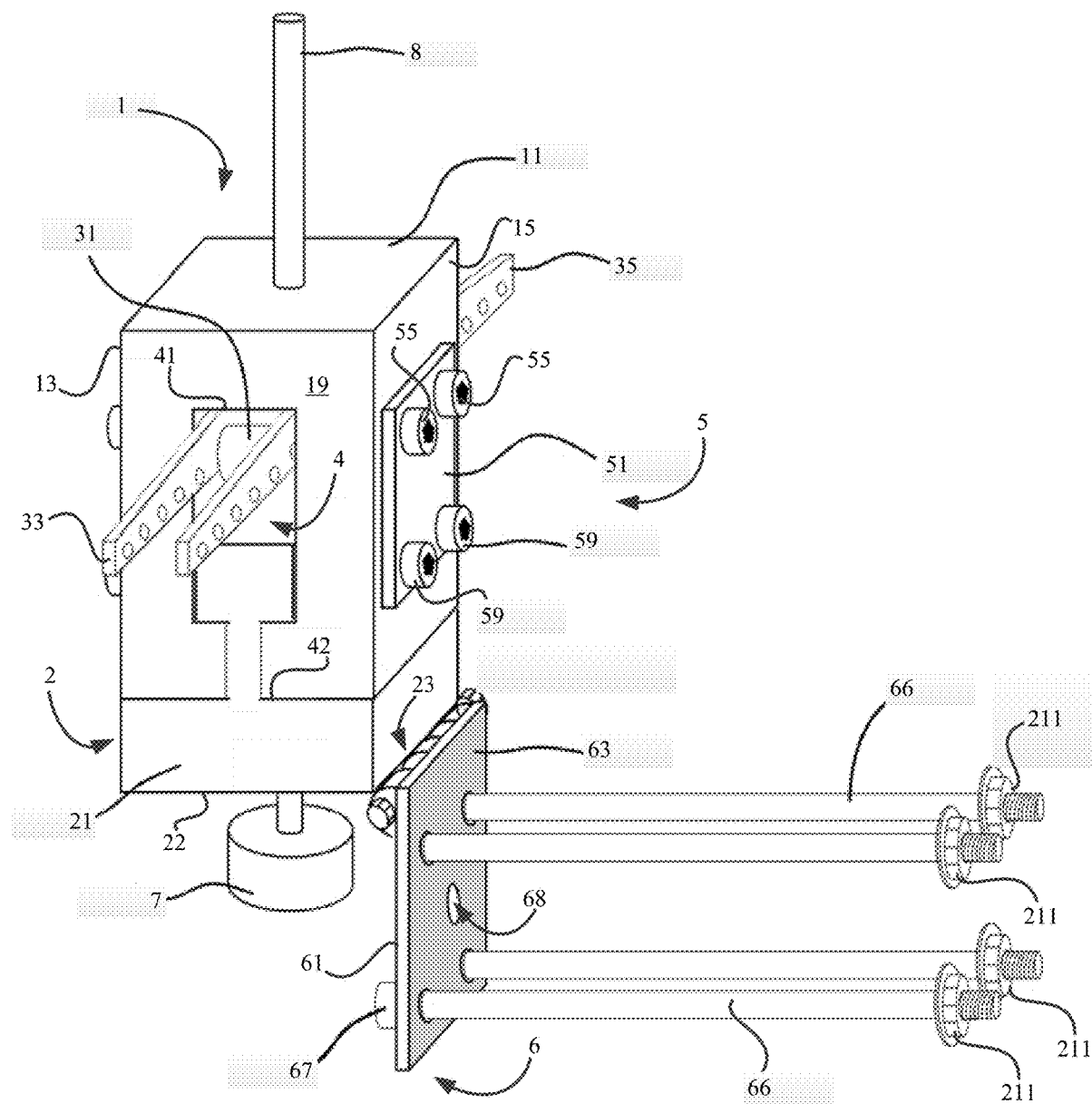
FIG. 6 is a perspective view of a preferred embodiment of the test apparatus described in the present disclosure.
Figure 7:
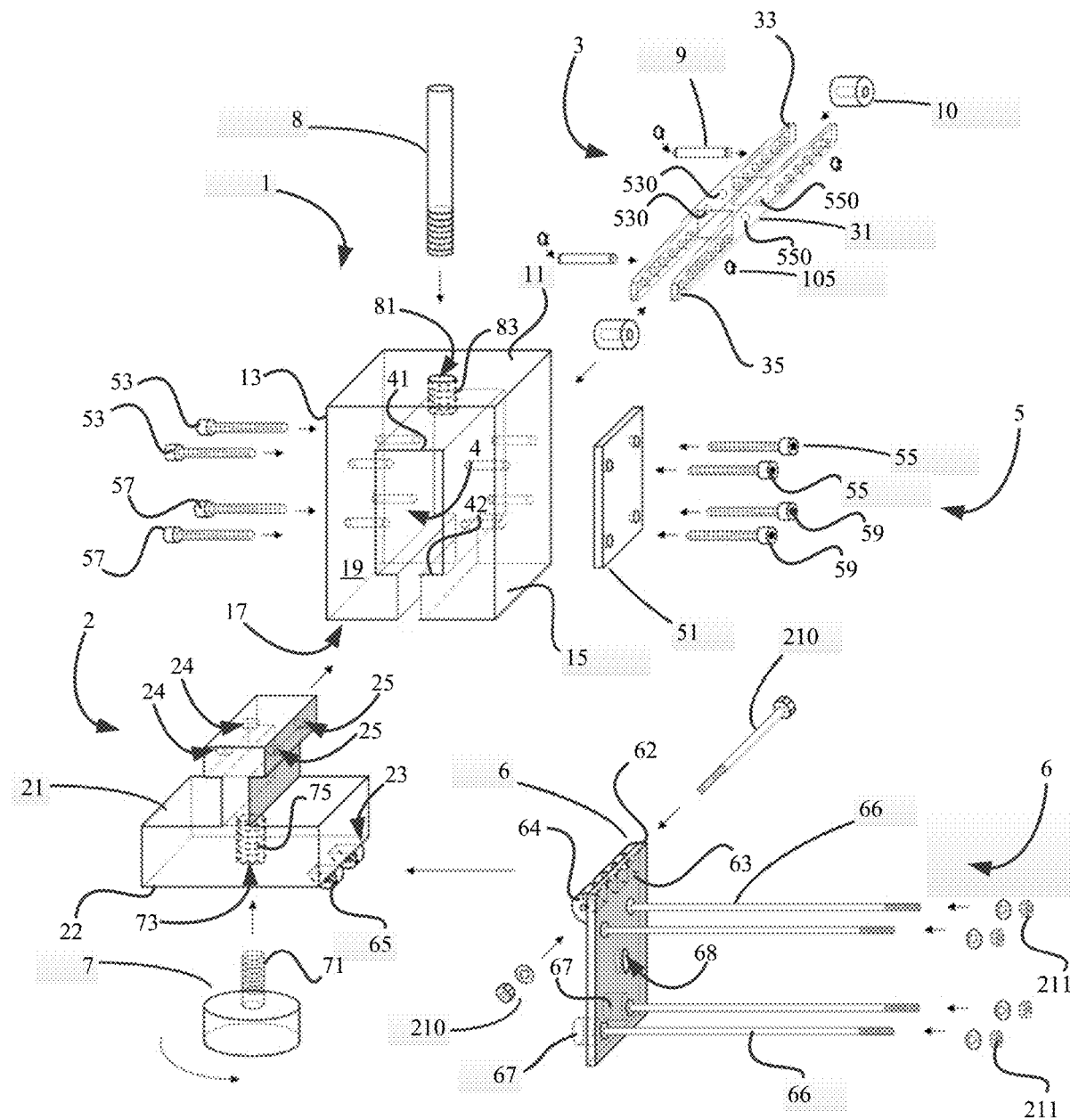
FIG. 7 is a perspective exploded view of a preferred embodiment of the test apparatus described in the present disclosure.

As illustrated in FIG. 6 and FIG. 7, to fulfill the intended functionalities, the test apparatus described in the present disclosure comprises a primary structural block 1 having a receiving slot 4, a secondary structural block 2, an adjustable hanger 3, and an attachment mechanism 5 which are manipulated to convert the test apparatus of the present disclosure to perform different test types on a CFRP-concrete bond. The primary structural block 1 and the secondary structural block 2 are used during single-shear testing, double-shear testing, mixed-mode testing, tension pull-off testing, and beam-bend testing. The primary structural block 1, which is preferably rectangular in shape, comprises a top surface 11, a first lateral surface 13, a second lateral surface 15, a bottom surface 17, and a structural body 19. The structural body 19 of the primary structural block 1 extends from the top surface 11 to the bottom surface 17 in between the first lateral surface 13 and the second lateral surface 15. Thus, a distance from the top surface 11 to the bottom surface 17 gives a height of the primary structural block 1 and a distance from the first lateral surface 13 to the second lateral surface 15 gives a width of the primary structural block 1.

The receiving slot 4 is used to position the secondary structural block 2 within the structural body 19 of the primary structural block 1. To do so, the receiving slot 4 traverses through the structural body 19 of the primary structural block 1 in between the first lateral surface 13 and the second lateral surface 15 adjacent the bottom surface 17 of the primary structural block 1. Therefore, the secondary structural block 2 can be slidably positioned into the receiving slot 4 along the bottom surface 17 of the primary structural block 1. The receiving slot 4 is configured to match a shape of a portion of the secondary structural block 2. In a preferred embodiment, a bottom portion of the receiving slot 4 is configured into a T-shape to receive a top portion of the secondary structural block 2 which has a T-shape. When slidably positioned into the receiving slot 4, the secondary structural block 2 is positioned adjacent a bottom end 42 of the receiving slot 4.

The height, length, and width of the primary structural block 1 and the secondary structural block 2 can vary from one embodiment to another. For example, in one embodiment a width, a length, and a height of the primary structural block 1 can be 120-millimeter (mm), 100 mm, and 170 mm respectively. To be used with the primary structural block 1 of the example, the secondary structural block 2 includes or consists of a base portion that is 100 mm in length and 30 mm in height. Thus, the primary structural block 1 and the secondary structural block 2 create an assembly with a height of 200 mm, a length of 100 mm, and a width of 120 mm. The concrete prism used with the assembly will also have the same height, length, and width as the assembly. Even though specific dimensions were described in the example, a wide range of dimensions can be used with the components of the debonding test apparatus since the concrete prism is not limited in size or shape.

The adjustable hanger 3, which is primarily used during double-shear testing and mixed mode testing, is also slidably positioned into the receiving slot 4. However, the adjustable hanger 3 is positioned adjacent a top end 41 of the receiving slot 4 such that the adjustable hanger 3 is positioned atop the secondary structural block 2 opposite the bottom end 42. The attachment mechanism 5 is used to hold the primary structural block 1, the secondary structural block 2, and the adjustable hanger 3 together during testing procedures. In particular, the primary structural block 1, the secondary structural block 2, and the adjustable hanger 3 are detachably attached through the attachment mechanism 5 that can vary in different embodiments of the present disclosure.

Figure 9:
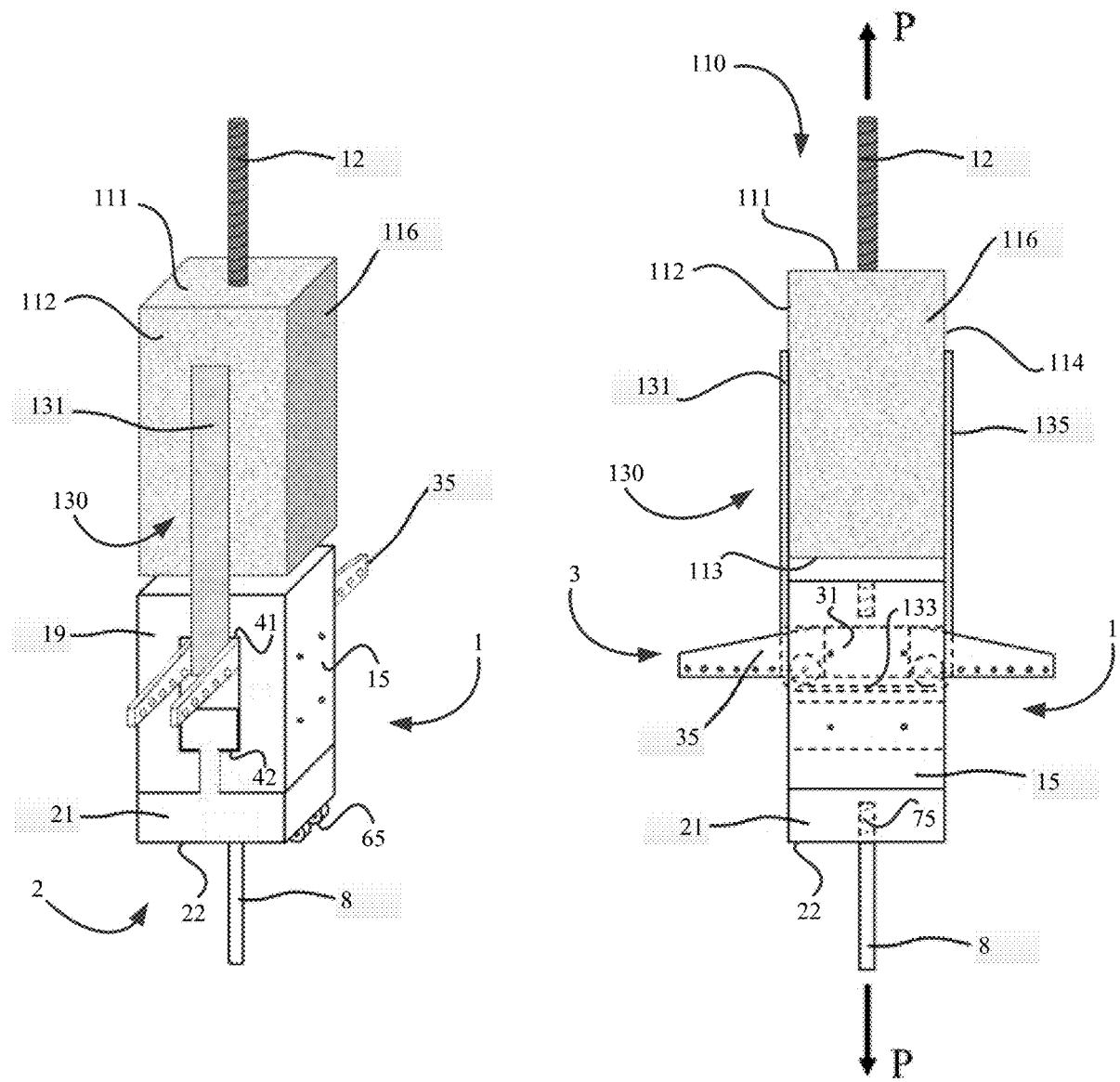
FIG. 9 is a perspective view and a side view illustrating the test apparatus of the present disclosure being used for double-shear testing with a U-shaped CFRP strip, wherein the adjustable hanger is in an upright configuration.

As shown in FIG. 9, when the test apparatus of the present disclosure is used for double-shear testing, a concrete prism 110 with a U-shaped CFRP strip 130 is provided. The concrete prism 110 is preferably cubical in shape.

In general, the concrete prism 110, which may also be referred to as a concrete prism or a concrete block, is cast from a suitably designed concrete grade. After sufficient setting time, the concrete prism 110 is demolded and cured in water for a specific time period. The curing time selected for the concrete prism 110 can vary according to user preferences and concrete standards that need to be fulfilled. The concrete prism 110 is allowed to dry for another time interval under ambient conditions. Next, the concrete prism 110 is prepared in order to establish a connection with a CFRP section which can vary according to the test conducted with the debonding test apparatus. For example, the CFRP section used for double-shear testing is different from the CFRP section used for single-shear testing. Different methods that can be, but is not limited to, using a grinding machine, air blasting, or sand blasting are used during the concrete prism 110 preparation process. Using methods such as the grinding machine helps remove any laitance and weak layers of the concrete prism 110 until the aggregates are exposed to provide a secure bond between adhesive and the concrete, wherein adhesive is used to attach the CFRP section to the concrete prism 110. After the preparation process is complete, prior to applying the adhesive, any dust that can be present on the concrete prism 110 is removed through air blasting. Next, an adhesive layer of uniform thickness and width is applied on the prepared external surface of the concrete prism 110, and the CFRP section that needs to be connected to the concrete prism 110 is attached. The CFRP section will have the same width as the adhesive layer. The CFRP section will have a length sufficient to allow unhindered mounting to the debonding test apparatus of the present disclosure. When the CFRP section is firmly attached to the concrete prism 110 through the adhesive layer, the debonding test apparatus of the present disclosure is used to perform different tests on the CFRP section attached to the concrete prism 110.

The U-shaped CFRP strip 130 is connected to the concrete prism 110 such that a first end 131 of the U-shaped CFRP strip 130 is attached onto a front surface 112 of the concrete prism 110. A second end 135 of the U-shaped CFRP strip 130 is attached onto a rear surface 114 of concrete prism 110. A base portion 133 of the U-shaped CFRP strip 130 is offset from and positioned in parallel to a second surface 113 of the concrete prism 110. The positioning of the second surface 113 is such that, both the front surface 112 and the rear surface 114 of the concrete prism 110 are perpendicular to the second surface 113 of the concrete prism 110. For load application purposes during the double-shear testing process, a loading rebar 12 centrally penetrates into a first surface 111 of the concrete prism 110. Preferably, the loading rebar 12 is inserted during casting of the concrete prism 110. Similar to the second surface 113, the first surface 111 is also perpendicular to the front surface 112 and the rear surface 114. However, the first surface 111 is positioned opposite the second surface 113 across a structural body of the concrete prism 110.

In order to perform the double-shear test on the U-shaped CFRP strip 130, the adjustable hanger 3 is slidably positioned into the receiving slot 4 adjacent the top end 41. As seen in the side view of FIG. 9, the adjustable hanger 3 is positioned in an upright configuration such that a central block 31 of the adjustable hanger 3 is surrounded by the structural body 19 of the primary structural block 1. Next, the base portion 133 is positioned into the receiving slot 4 through the bottom surface 17 of the primary structural block 1. The upright configuration allows the base portion 133 to be wrapped around the central block 31. In particular, the base portion 133 is positioned in between the top end 41 and the bottom end 42 of the receiving slot 4 and wrapped around the central block 31 of the adjustable hanger 3. Next, the secondary structural block 2 is slidably positioned into the receiving slot 4 such that the base portion 133 is positioned in between the secondary structural block 2 and the adjustable hanger 3. When the base portion 133 is wrapped around the central block 31 and the secondary structural block 2 is positioned as required, a threaded gripping rod 8 is threadably engaged into a bottom-receiving channel 73, wherein the bottom-receiving channel penetrates into a bottom surface 22 of the secondary structural block 2. The threaded gripping rod 8 is threadably engaged with a plurality of threads 75 that is internally distributed along the bottom-receiving channel 73. As a final step, a first load is applied along the loading rebar 12 and a second load is applied along threaded gripping rod 8 simultaneously. The first load is equal in magnitude to the second load but is opposite in direction. Since the attachment mechanism 5 holds the primary structural block 1, the adjustable hanger 3, and the secondary structural block 2 stationary during the testing process, the U-shaped CFRP strip 130 trapped in between the adjustable hanger 3 and the secondary structural block 2 also remains stationary. The first load and the second load can be applied through a loading machine which can be, but is not limited to, a universal testing machine (UTM). The first load and the second load are varied to measure a shear load, wherein the shear load is when the double-shearing occurs in the U-shaped CFRP strip 130. In addition to the shear load so measured, other means of data acquisition sensors such as strain gauges and/or linear variable transducers may be used on the bonded portion between the U-shaped CFRP strip and the concrete prism to record strain and/or loaded end displacements for further analysis.

Figure 10:
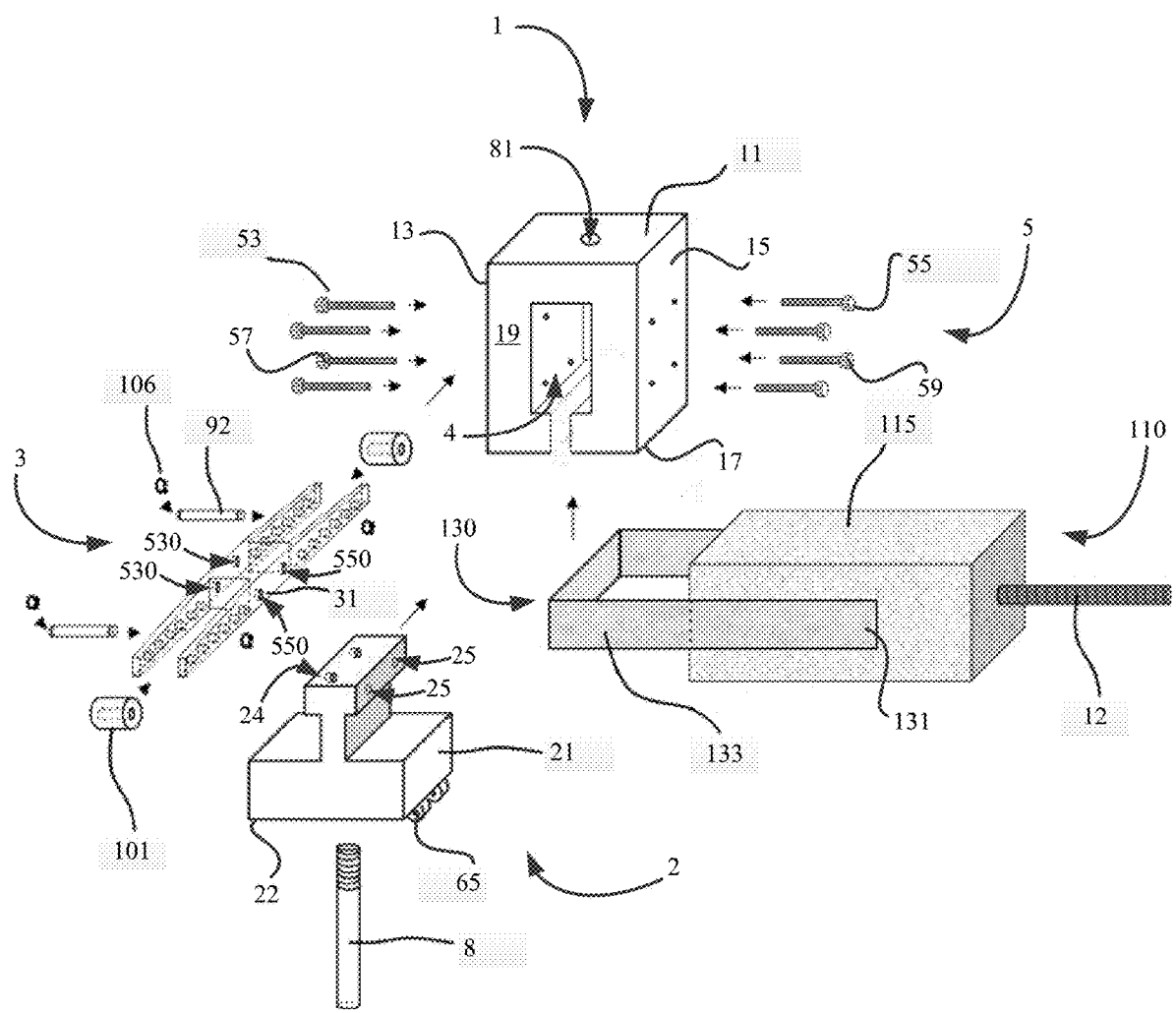
FIG. 10 is a perspective exploded view of the test apparatus of the present disclosure being used for double-shear testing with the U-shaped CFRP strip.

As discussed earlier, the attachment mechanism 5 used to hold the primary structural block 1, the secondary structural block 2, and the adjustable hanger 3 together can vary from one embodiment to another. The attachment mechanism also aids in holding a planar CFRP strip 14 against the primary structural block 1 during single-shear testing and beam-bend testing. As seen in FIG. 7, in a preferred embodiment of the present disclosure, the attachment mechanism 5 comprises a first pair of hanger-fastening bolts 53, a second pair of hanger-fastening bolts 55, a first pair of block-fastening bolts 57, and a second pair of block-fastening bolts 59. As seen in FIG. 10, when the adjustable hanger 3 is slidably positioned into the receiving slot 4, the first pair of hanger-fastening bolts 53 traverses through the first lateral surface 13 of the primary structural block 1 and presses into and against the first pair of hanger bolt-receiving slots 530 serving as receptacles on the side of the central block 31 of the adjustable hanger 3. When the secondary structural block 2 is slidably positioned into the receiving slot 4, the first pair of block-fastening bolts 57 traverses through the first lateral surface 13 of the primary structural block 1 and presses into and against the first pair of block bolt-receiving slots 24 serving as receptacles on a side of a structural body 21 of the secondary structural block 2. Since the adjustable hanger 3 is positioned atop the secondary structural block 2, the first pair of hanger-fastening bolts 53 is positioned above the first pair of block-fastening bolts 57. Opposite the first lateral surface 13, the second pair of hanger-fastening bolts 55 traverses through a second lateral surface 15 of the primary structural block 1 and presses into and against the second pair of hanger bolt-receiving slots 550 on an opposite side of the central block 31 of the adjustable hanger 3. In a final configuration, the first pair of hanger-fastening bolts 53 and the second pair of hanger-fastening bolts 55 will be positioned on either side of the central block 31. On the other hand, the second pair of block-fastening bolts 59 traverses through the second lateral surface 15 and presses into and against block bolt-receiving slots 25 serving as receptacles on an opposite side the structural body 21 of the secondary structural block 2. In a final configuration, the second pair of block-fastening bolts 59 and the first pair of block-fastening bolts 57 will be positioned on either side of the structural body 21 of the secondary structural block 2.

As shown in FIG. 7, to minimize eccentricity when performing double-shear tests, to perform single-shear tests, tension pull-off tests, and beam-bend tests, the test apparatus of the present disclosure further comprises a connecting plate 6 having a circular opening 68, a first plurality of hinges 64, a second plurality of hinges 65, and a plurality of rods 66. The first plurality of hinges 64 and the second plurality of hinges 65 are used to mount the connecting plate 6 to a bottom surface 22 of the secondary structural block 2. The overall dimensions of the connecting plate 6 are selected to match the overall dimensions of the bottom surface 22 of the secondary structural block 2. For example, if the bottom surface 22 of the secondary structural block 2 is rectangular in shape, the connecting plate 6 will also be rectangular in shape with similar dimensions. The circular opening 68 centrally traverses through the connecting plate 6 such that a threaded protrusion 71 can be positioned into the circular opening 68 and through the connecting plate 6. The first plurality of hinges 64 is laterally positioned along a length 62 of a first surface 61 of the connecting plate 6. To engage with the first plurality of hinges 64, the second plurality of hinges 65 is positioned along a length 23 of the bottom surface 22 of the secondary structural block 2. Thus, the connecting plate 6 can be hingedly connected to the bottom surface 22 of the secondary structural block 2 by engaging the first plurality of hinges 64 with the second plurality of hinges 65 using a first set of fastening nuts/washers 210. In other words, the first plurality of hinges 64 and the second plurality of hinges 65 are engageable with one another in such a way that the connecting plate 6 is connected to the bottom surface 22 of the secondary structural block 2. The hinged connection between the connecting plate 6 and the secondary structural block 2 allows an operational-angle between the bottom surface 22 of the secondary structural block 2 and the first surface 61 of the connecting plate 6 to be adjusted as preferred. The plurality of rods 66 is used to establish a connection with a concrete specimen during testing procedures. The plurality of rods 66 is also used as a guide path during load application. To do so, the plurality of rods 66 is perpendicularly connected to a second surface 63 of the connecting plate 6, wherein the second surface 63 is positioned opposite the first surface 61 of the connecting plate 6. The positioning of the first surface 61 and the second surface 63 is such that a distance between the first surface 61 and the second surface 63 determines a thickness of the connecting plate 6. Since the plurality of rods 66 is connected to the connecting plate 6, the orientation of the plurality of rods 66 can be manipulated by adjusting the operational-angle using the first plurality of hinges 64 and the second plurality of hinges 65. A pair of optional stoppers 67 is used to maintain a gap between the bottom surface 22 of the secondary structural block 2 and the first surface 61 of the connecting plate 6. In particular, the optional stoppers 67 ensure that the bottom surface 22 of the secondary structural block 2 and the first surface 61 of the connecting plate 6 are positioned in parallel to each other. To do so, the pair of optional stoppers 67 extends from the first surface 61 opposite and adjacent the first plurality of hinges 64. The pair of optional stoppers 67 is also used to eliminate any relative movement between the primary structural block 2 and the connecting plate 6 during testing procedures.

Figure 11:
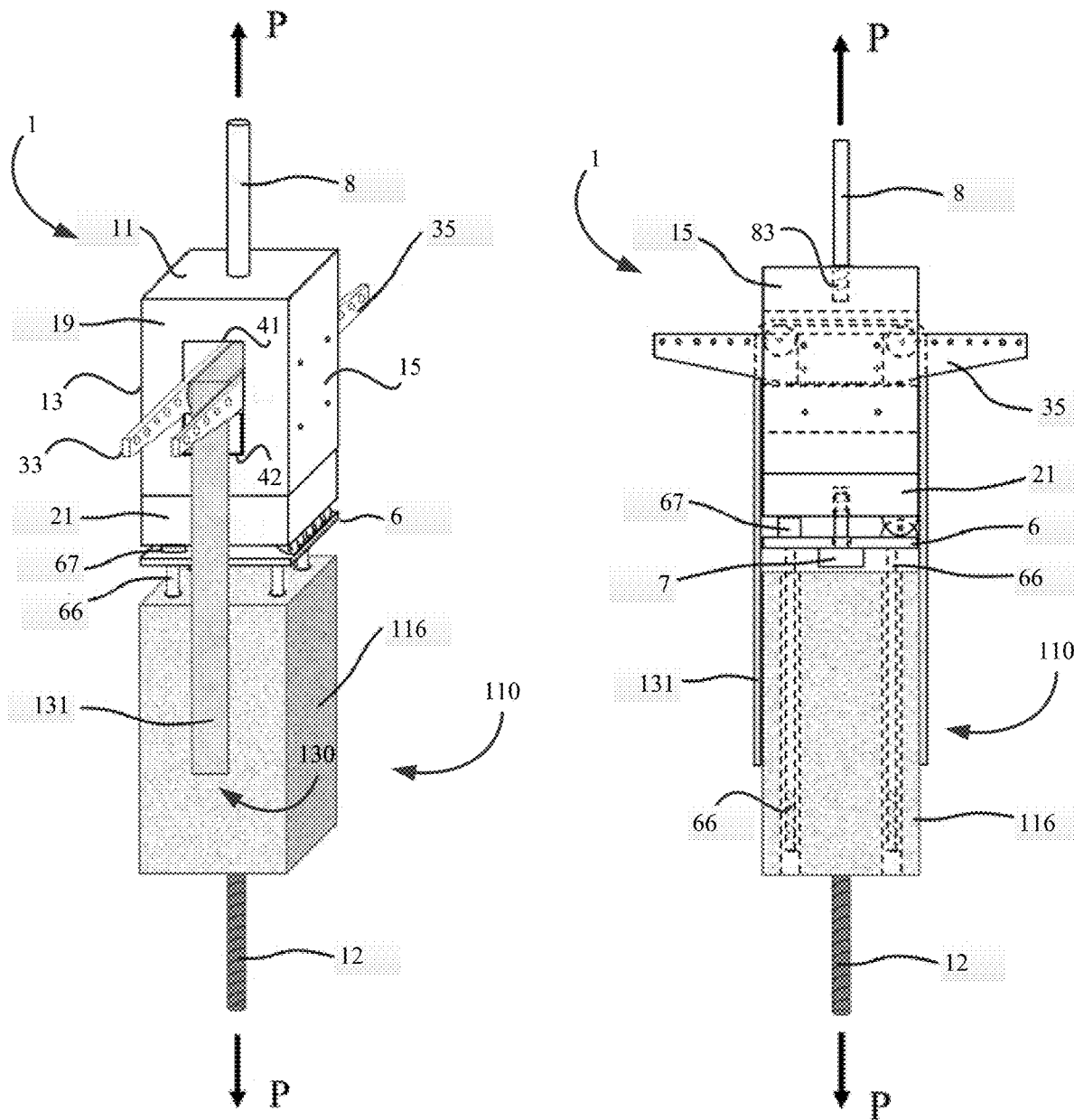
FIG. 11 is perspective view and a side view illustrating the test apparatus of the present disclosure being used for double-shear testing with a U-shaped CFRP strip, wherein eccentricity is minimized through a plurality of rods and the adjustable hanger is in a flipped configuration.

As seen in FIG. 11, when utilizing the test apparatus of the present disclosure to minimize eccentricity of the double-shear test, the base portion 133 of the U-shaped CFRP strip 130 is positioned adjacent the top end 41 of the receiving slot 4. Moreover, the base portion 133 is positioned such that the first end 131 and the second end 135 of the U-shaped CFRP strip 130 are oriented towards the bottom end 42 of the receiving slot 4. Next, the adjustable hanger 3 is positioned adjacent the base portion 133 and opposite the top end 41 in a flipped configuration. The flipped configuration, as seen in the side view of FIG. 11, allows the base portion 133 to be wrapped around the central block 31 of the adjustable hanger 3. Next, the secondary structural block 2 is slidably positioned into the receiving slot 4 such that the adjustable hanger 3 is positioned in between the base portion 133 and the secondary structural block 2. In order to establish a connection with the concrete prism 110, which already houses the plurality of rods 66 extending from the connecting plate 6, which in turn has the threaded protrusion 71 connected to the tension pull-off disk 7 positioned through the circular opening 68, the connecting plate 66 is pivoted towards the bottom surface 22 of the secondary structural block 2 such that the pair of optional stoppers 67 is pressed against the bottom surface 22 of the secondary structural block 2. The first set of fastening nuts/washers 210 is used to couple the first plurality of hinges 64 and the second plurality of hinges 65. In addition, the tension pull-off disk 7 is used to secure and fix in place the connecting plate 6 by threading the threaded protrusion 71 connected to the tension pull-off disk 7 into the bottom-receiving channel traversing a bottom surface 22 of the secondary structural block 2. As mentioned earlier, the plurality of rods 66 extending from the second surface 63 of the connecting plate 6 is positioned through a second surface 113 of the concrete prism 110 establishing a connection between the connecting plate 6 and the concrete prism 110. In particular, the plurality of rods 66 ensures that the load application is performed in a linear path. To do so, the plurality of rods is preferably positioned into a set of hollow plastic pipes that is vertically embedded within the concrete prism 110. Thus, relative lateral movement between the secondary structural block 2 and the connecting plate 6 is minimized. For load application purposes, a threaded gripping rod 8 is threadably engaged into a top-receiving channel 81 that traverses into a top surface 11 of the primary structural block 1. In particular, the threaded gripping rod 8 is threadably engaged with a plurality of threads 83 that is internally distributed along the top-receiving channel 81. As a final step, a first load is applied along the loading rebar 12 and a second load is applied along the threaded gripping rod 8 simultaneously. The first load is substantially equal in magnitude to the second load but is opposite in direction. Since the attachment mechanism 5 holds the primary structural block 1, the adjustable hanger 3, and the secondary structural block 2 stationary during the testing process, the U-shaped CFRP strip 130 trapped in between the adjustable hanger 3 and top end 41 of the receiving slot 4 also remains stationary. The first load and the second load can be applied through a loading machine which can be, but is not limited to, a universal testing machine (UTM). The first load and the second load are managed to measure a shear load, wherein the shear load is when the double-shearing occurs in the U-shaped CFRP strip 130. Similar to the previous instance wherein the adjustable hanger 3 was in the upright configuration, the first pair of hanger-fastening bolts 53, the second pair of hanger-fastening bolts 55, the first pair of block-fastening bolts 57, and the second pair of block-fastening bolts 59 can be used to secure the primary structural block 1, the adjustable hanger 3, and the secondary structural block 2. Also, in addition to the shear load measured other means of data acquisition sensors such as strain gauges and/or linear variable transducers may be used on the bonded portion between the U-shaped CFRP strip and the concrete prism 110 to record strain and/or loaded end displacements for further analysis.

Figure 12:
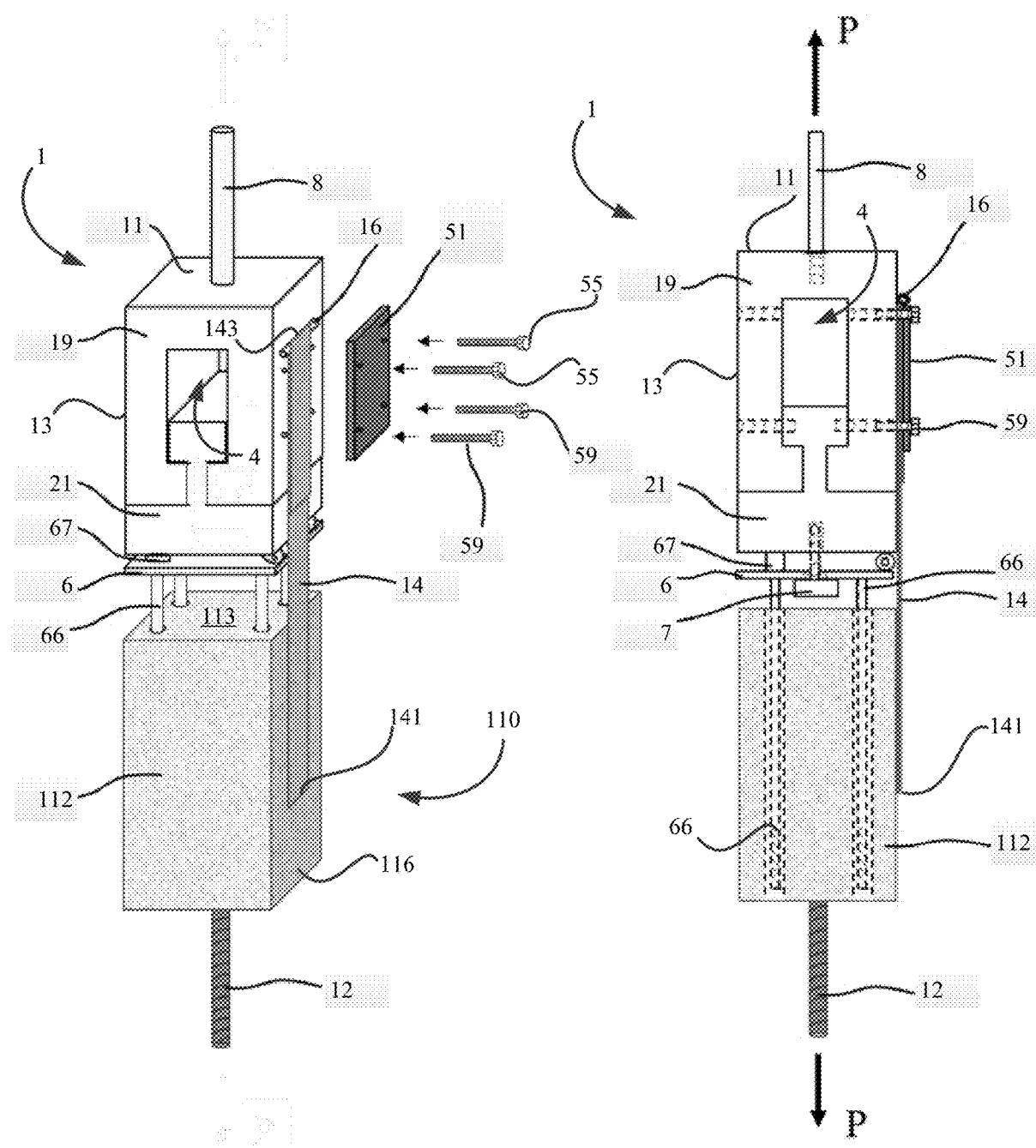
FIG. 12 is a perspective view and a side view illustrating the test apparatus of the present disclosure being used for single-shear testing with a planar CFRP strip.

As shown in FIG. 12, in order to perform the single-shear test, a concrete prism 110 with a planar CFRP strip 14 is provided. A first end 141 of the planar CFRP strip 14 is adhered to a second lateral surface 116 of the concrete prism 110 and a body portion of the planar CFRP strip 14 is folded over the anchor rod 16 and an overlapping portion of the planar CFRP strip 14 is glued together. The overlapping portion resulting in an overlapping end 143 is fixed to a second lateral surface 15 of the primary structural block 1 using the attachment mechanism 5 during the testing process. For load application purposes, a loading rebar 12 centrally penetrates into a first surface 111 of the concrete prism 110. When performing the single-shear test, the secondary structural block 2 is positioned within the receiving slot 4 and the connecting plate 6, already coupled with the secondary structural block 2 using the first plurality of hinges 64 and the second plurality of hinges 65, is pivoted towards the bottom surface 22 of the secondary structural block 2 such that the pair of optional stoppers 67 is pressed in between the bottom surface 22 of the secondary structural block 2 and the first surface 61 of the connecting plate 6. Thus, the first surface 61 of the connecting plate 6 will be positioned in parallel to the bottom surface 22 of the secondary structural block 2. In addition, the tension pull-off disk 7 is used to secure and fix in place the connecting plate 6 by positioning the threaded protrusion 71 through the circular opening 68 and into the bottom-receiving channel 73 traversing into the bottom surface 22 of the secondary structural block 2. The plurality of rods 66 extending from the second surface 63 of the connecting plate 6 is slidably positioned through the second surface 113 of the concrete prism 110.

The overlapping end 143 of the planar CFRP strip 14 is secured against the second lateral surface 15 of the primary structural block 1 through an attachment plate 51 which is mounted onto the second lateral surface 15 of the primary structural block 1 using the attachment mechanism 5. The attachment plate 51 is mounted such that a body portion of planar CFRP strip 14 is positioned in between the attachment plate 51 and the second lateral surface 15. The attachment plate 51 is positioned adjacent the overlapping end 143 of the planar CFRP strip 14 and the anchor rod 16. Hence, the anchor rod 16 over which a second end of the CFRP strip is folded acts as a further stopper by wedging against the attachment plate 51 of the attachment mechanism 5. For load application purposes, a threaded gripping rod 8 is threadably engaged into a top-receiving channel 81 traversing into a top surface 11 of the primary structural block 1. In particular, the threaded gripping rod 8 is threadably engaged with a plurality of threads 83 that is internally distributed along the top-receiving channel 81. For testing purposes, a first load is applied along the loading rebar 12 and a second load is applied along threaded gripping rod 8 simultaneously. The first load is substantially equal in magnitude to the second load but is opposite in direction. The first load and the second load are managed to measure a shear load, wherein the shear load is when the shearing occurs in the planar CFRP strip 14. In addition to the shear load so measured, other means of data acquisition sensors such as strain gauges and/or linear variable transducers may be used on the bonded portion between the planar CFRP strip and the concrete prism 110 to record strain and/or loaded end displacements for further analysis.

As discussed earlier, the attachment plate 51 used for holding the planar CFRP strip 14 against the second lateral surface 15 is mounted through the attachment mechanism 5. In doing so, the second pair of hanger-fastening bolts 55 traverses through the attachment plate 51 and the second lateral surface 15. On the other hand, the second pair of block-fastening bolts 59 traverses through the attachment plate 51 and the second lateral surface 15, and presses into and against the second pair of block bolt-receiving slots 25 on a side of the structural body 21 of the secondary structural block 2. The planar CFRP strip 14 is positioned through the second pair of hanger-fastening bolts 55 and the second pair of block-fastening bolts 59. The spacing between each of the second pair of hanger-fastening bolts 55 and each of the second pair of block-fastening bolts 59 allows the planar CFRP strip 14 to be positioned through the second pair of hanger-fastening bolts 55 and the second pair of block-fastening bolts 59.

Figure 13:
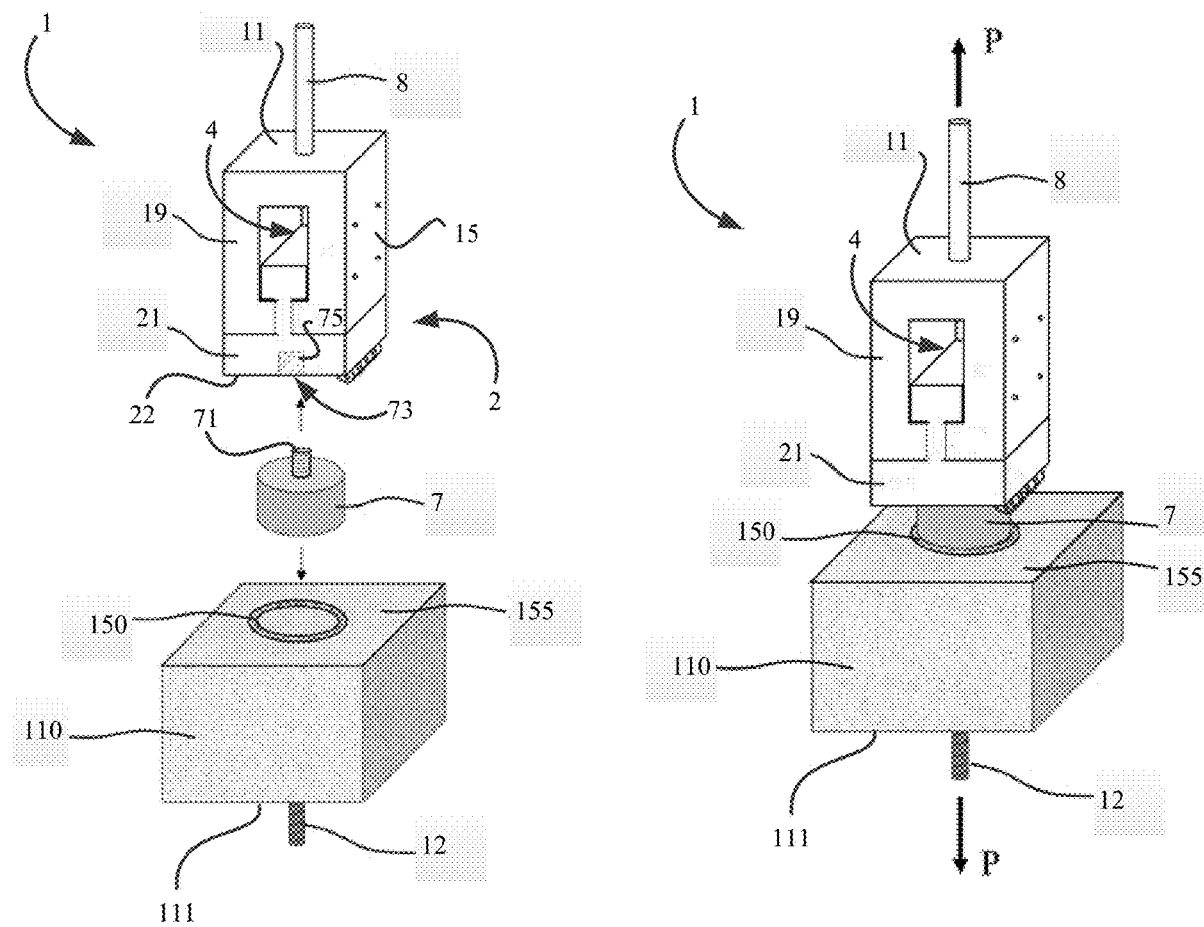
FIG. 13 is a perspective exploded view and a perspective view illustrating the test apparatus of the present disclosure being used for tension pull-off testing with a CFRP sheet.

As illustrated in FIG. 13, in order to perform the tension pull-off tests, the test apparatus described in the present disclosure further comprises a tension pull-off disk 7, a threaded protrusion 71, and a bottom-receiving channel 73. The tension pull-off disk 7 and the threaded protrusion 71 function as a single unit where the threaded protrusion 71 is perpendicularly connected to a structural body of the tension pull-off disk 7. The bottom-receiving channel 73 perpendicularly traverses into the bottom surface 22 of the secondary structural block 2. Therefore, in order to establish a connection with the secondary structural block 2, the threaded protrusion 71 is threadably engaged with a plurality of threads 75 of the bottom-receiving channel 73. To do so, the plurality of threads 75 is internally distributed along the bottom-receiving channel 73. When the tension pull-off disk 7 is not connected to the bottom surface 22 of the secondary structural block 2, a threaded gripping rod 8 can be positioned into the bottom-receiving channel 73 through the plurality of threads 75 such as in the case of the double-shear test.

In order to perform the tension pull-off test, a concrete prism 110 with a CFRP sheet 155 is provided. The CFRP sheet 155 is adhered to a second surface 113 of the concrete prism 110 and matches the overall shape of the concrete prism 110. A circular channel 150 that traverses into the second surface 113 through the CFRP sheet 155 is used as the testing area for the tension pull-off test. Similar to the previous tests, a loading rebar 12 centrally penetrates into a first surface 111 of the concrete prism 110 for load application purposes. In order to perform the tension pull-off test, the tension pull-off disk 7 is pressed and adhered onto the CFRP sheet 155 such that the tension pull-off disk 7 is concentrically aligned with the circular channel 150. In particular, a surface opposite to the threaded protrusion 71 is adhered to a CFRP sheet 155 portion surrounded by the circular channel 150. To apply a load at the primary structural block 1, a threaded gripping rod 8 is threadably engaged with a plurality of threads 83 of a top-receiving channel 81 that traverses into a top surface 11 of the primary structural block 1. To do so, the plurality of threads 83 is internally distributed along the top-receiving channel 81. To execute the tension pull-off test, a first load is applied along the loading rebar 12 and a second load is simultaneously applied along the threaded gripping rod 8. The first load is substantially equal in magnitude and opposite in direction to the second load. The first load and the second load are managed to measure a pull-off load, wherein the pull-off load corresponds to when the debonding occurs between the CFRP sheet 155 and the concrete prism 110.

As mentioned earlier and as illustrated in FIG. 8, the adjustable hanger 3 is used when double-shear testing and mixed-mode testing is performed with the test apparatus described in the present disclosure. To fulfill the requirements of both the double-shear test and the mixed-mode test, the adjustable hanger 3 comprises a central block 31, a first arm portion 33, a second arm portion 35, and a plurality of receiving slots 37. The central block 31 is centrally positioned in between the first arm portion 33 and the second arm portion 35 such that a uniform gap is maintained between the first arm portion 33 and the second arm portion 35 on either side of the central block 31.

Figure 14:
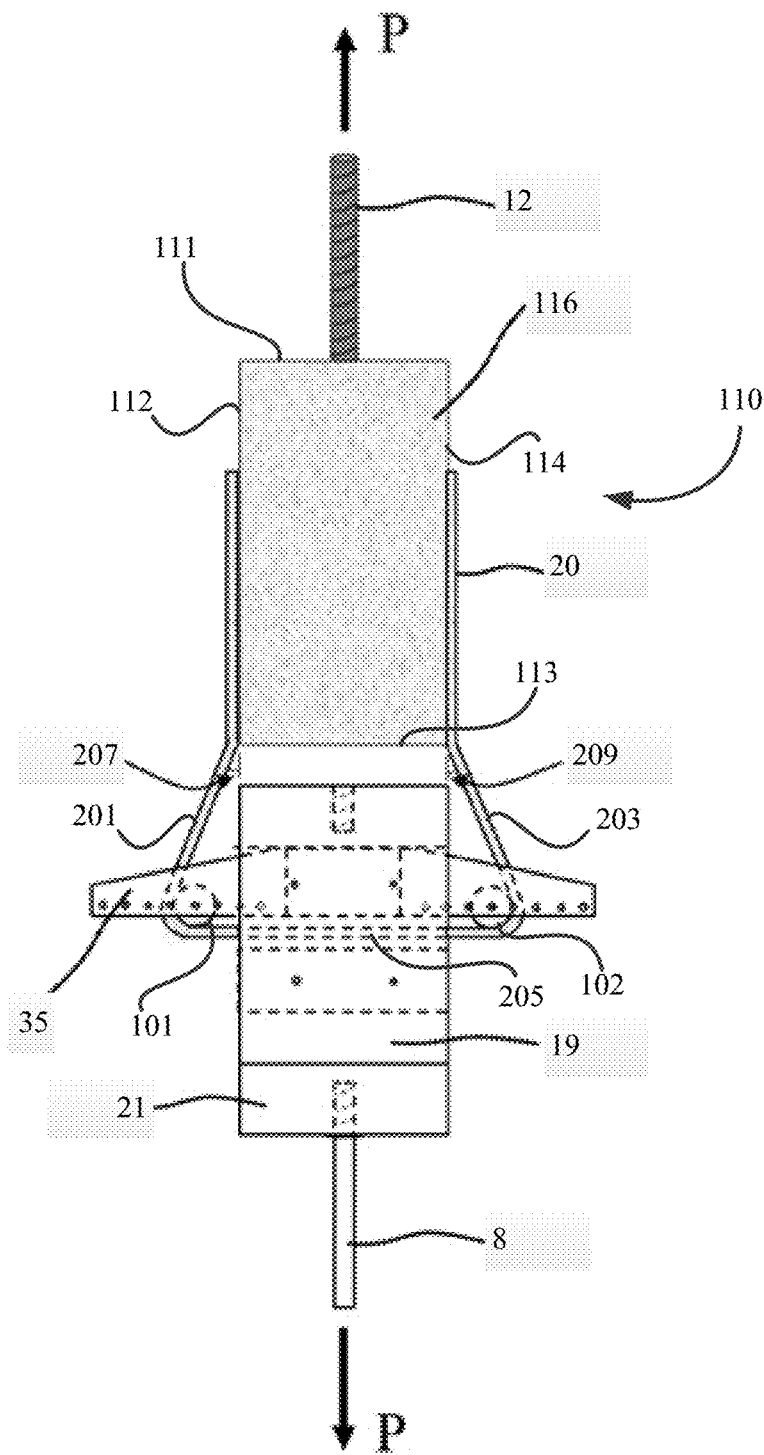
FIG. 14 is a side view illustrating the test apparatus of the present disclosure being used to analyze shearing and peeling effects of a trapezoidal-based CFRP strip.
Figure 15:
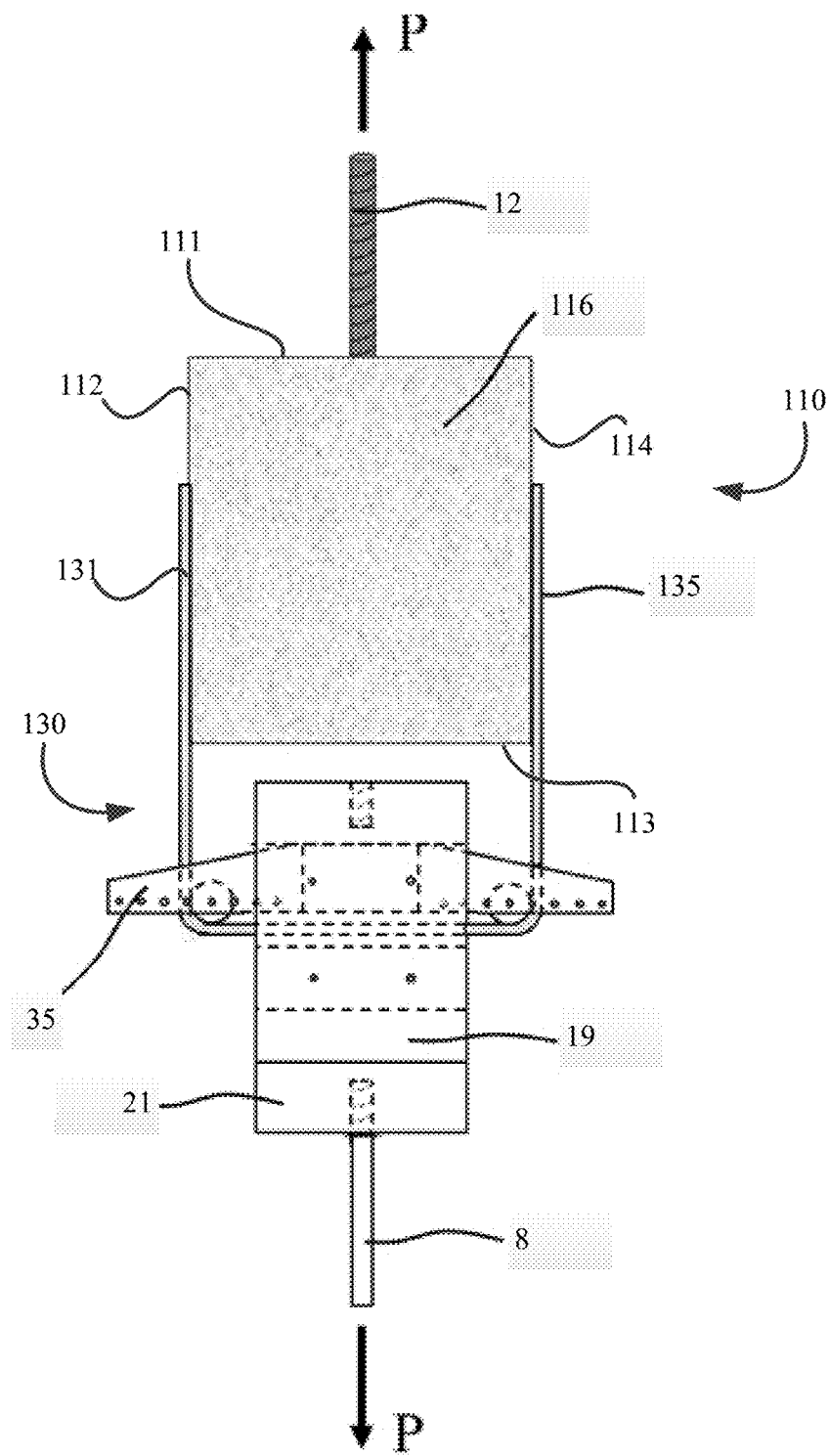
FIG. 15 is a side view illustrating the test apparatus of the present disclosure being used to analyze double-shearing, wherein an adjustable hanger allows differently sized concrete specimens to be tested.

As illustrated in FIG. 14 and FIG. 15, the plurality of receiving slots 37 is used to accommodate differently sized concrete blocks during double-shear testing and is also used during mixed-mode testing. To do so, the plurality of receiving slots 37 perpendicularly traverses through a structural body 36 of both the first arm portion 33 and the second arm portion 35 adjacent the central block 31. In a preferred embodiment, each of the plurality of receiving slots 37 is equidistantly distributed along a length of the first arm portion 33 and a length of the second arm portion 35, wherein the length of the first arm portion 33 is equivalent to the length of the second arm portion 35. Therefore, a selected receiving slot on the first arm portion 33 has a corresponding receiving slot on the second arm portion 35. Since each of the plurality of receiving slots 37 corresponds to a different length from a center of the central block 31, concrete blocks of different sizes can be used with the adjustable hanger 3. Moreover, varying peeling angles can also be examined by using the plurality of receiving slots 37 during mixed-mode testing.

Figure 8:
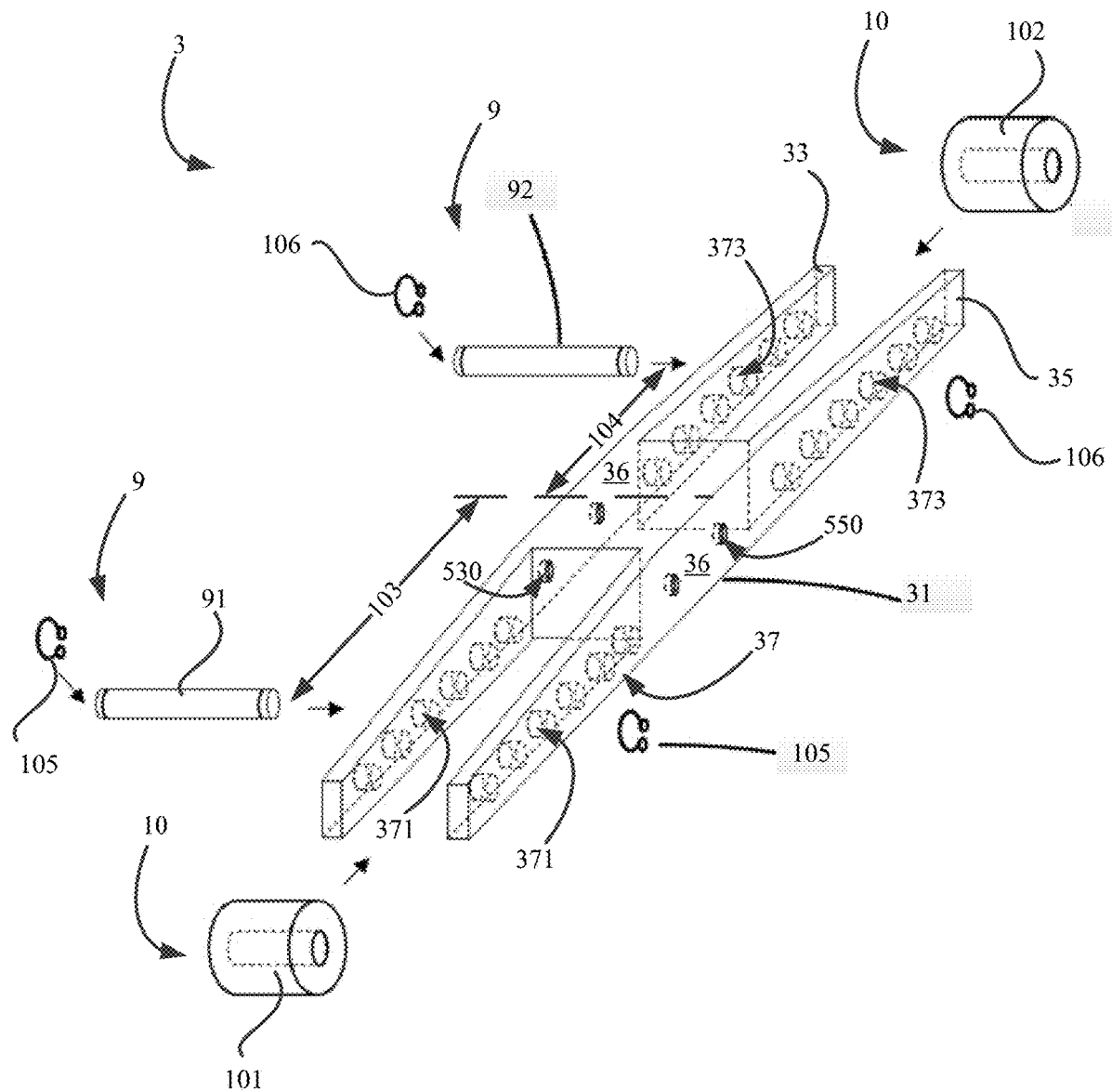
FIG. 8 is a perspective exploded view of the adjustable hanger, a pair of solid cylinders, and a pair of hollow cylinders, wherein the adjustable hanger is in an upright configuration.

As further illustrated in FIG. 8, the test apparatus of the present disclosure further comprises a pair of hollow cylinders 10 and a pair of solid cylinders 9 that are used to establish a secure connection between a CFRP test piece and the adjustable hanger 3. In particular, the test apparatus of the present disclosure utilizes the pair of solid cylinders 9 and the pair of hollow cylinders 10 to hold the CFRP test piece against the adjustable hanger 3 during double-shear testing and mixed-mode testing.

As discussed earlier, when the test apparatus is used for double-shear testing and mixed mode testing, a portion of the CFRP test-piece is positioned in between the first arm portion 33 and the second arm portion 35. If a first end of the CFRP test-piece needs to be positioned at a primary distance 103 from a center of the central block 31, a first hollow cylinder 101 from the pair of hollow cylinders 10 is positioned in between the first arm portion 33 and the second arm portion 35 at the primary distance 103. The first hollow cylinder 101 is also concentrically aligned with a first selected receiving slot 371 from the plurality of receiving slots 37. In this instance, the primary distance 103 is a linear distance measured from a center of the central block 31 to the first selected receiving slot 371. Next, a first solid cylinder 91 from the pair of solid cylinders 9 is also concentrically aligned with the first selected receiving slot 371. Next in order to position the first end of the CFRP test piece at the primary distance 103, the first solid cylinder 91 is slidably positioned through the first selected receiving slot 371 traversing the first arm portion 33, the first hollow cylinder 101, and the first selected receiving slot 371 traversing the second arm portion 35. The first solid cylinder 91 can be secured within the first hollow cylinder 101 through a first-fastening mechanism 105 that can be, but is not limited to, a first pair of circlips.

If a second end of the CFRP test piece, wherein the second end is positioned opposite the first end, needs to be positioned at a secondary distance 104 from a center of the central block 31, a second hollow cylinder 102 from the pair of hollow cylinders 10 is positioned in between the first arm portion 33 and the second arm portion 35. The second hollow cylinder 102 will be concentrically aligned with a second selected receiving slot 373 from the plurality of receiving slots 37. In this instance, the secondary distance 104 is a linear distance measured from a center of the central block 31 to the second selected receiving slot 373. Next, a second solid cylinder 92 from the pair of solid cylinders 9 is also concentrically aligned with the second selected receiving slot 373. Next, in order to position the second end of the CFRP test piece at the secondary distance 104, the second solid cylinder 92 is slidably positioned through the second selected receiving slot 373 traversing the first arm portion 33, the second hollow cylinder 102, and a second selected receiving slot 373 traversing the second arm portion 35. The second solid cylinder 92 can be secured within the second hollow cylinder 102 through a second-fastening mechanism 106 that can be, but is not limited to, a second pair of circlips. Preferably, the primary distance 103 is equivalent to the secondary distance 104.

When the test apparatus of the present disclosure is being used for double-shear testing, the primary distance 103 and the secondary distance 104 are selected to be minimal. In particular, the primary distance 103 and the secondary distance 104 are selected so that a body portion of the U-shaped CFRP strip 130 maintains the U-shape after being secured with the pair of solid cylinders 9 and the pair of hollow cylinders 10 as in FIG. 15. To minimize the primary distance 103 and the secondary distance 104, the closest slots on either side of the central block 31 are selected as the first selected receiving slot 371 and the second selected receiving slot 373.

As seen in FIG. 14, when the test apparatus of the present disclosure is being used for mixed-mode testing, wherein both shearing and peeling is analyzed, the primary distance 103 and the secondary distance 104 are selected to be greater than a width of the concrete prism 110 that is being used. The mixed-mode test is performed on a concrete prism 110 with a trapezoidal-based CFRP strip 20. A long base 205 of the trapezoidal-based CFRP strip 20 is offset and is positioned in parallel to a second surface 113 of the concrete prism 110. The trapezoidal-based CFRP strip 20 is connected to the concrete prism 110 such that a first leg 201 of the trapezoidal-based CFRP strip 20 is positioned at a first peeling angle 207 with a front surface 112 of the concrete prism 110. The connection between the trapezoidal-based CFRP strip 20 and concrete prism 110 ensures that a second leg 203 of the trapezoidal-based CFRP strip 20 is positioned at a second peeling angle 209 with a rear surface 114 of the concrete prism 110. As an initial step of performing the mixed-mode test, the adjustable hanger 3 is positioned into the receiving slot 4 in an upright configuration adjacent the top end 41. The long base 205 is then positioned in between and in parallel with the first arm portion 33 and the second arm portion 35 such that the trapezoidal-based CFRP strip 20 is oriented towards a top surface 11 of the primary structural block 1. The first selected receiving slot 371, positioned at the primary distance 103, is selected so that a base angle between the first leg 201 and the long base 205 is intersected by the first hollow cylinder 101 and the first solid cylinder 91. On the other hand, the second selected receiving slot 373, positioned at the secondary distance 104, is selected so that a base angle between the second leg 203 and the long base 205 is intersected by the second hollow cylinder 102 and the second solid cylinder 92. If the trapezoidal-based CFRP strip 20 is symmetrical, the primary distance 103 is equivalent to the secondary distance 104. However, if the CFRP test-piece used for mixed-mode testing is asymmetrical, the primary distance 103 can be different to the secondary distance 104. When the trapezoidal-based CFRP strip 20 is secured against the adjustable hanger 3, the secondary structural block 2 is slidably positioned into the receiving slot 4 such that the long base 205 is positioned in between the adjustable hanger 3 and the secondary structural block 2. To execute the mixed-mode test, a first load is applied along the loading rebar 12 and a second load is simultaneously applied along the threaded gripping rod 8, wherein the first load is substantially equal in magnitude to the second load and is opposite in direction. For load application purposes, the loading rebar 12 penetrates into a first surface 111 of the concrete prism 110. The first peeling angle 207 and the second peeling angle 209 are measured to analyze shearing and peeling according to the load applied as the first load and the second load. In addition, other means of data acquisition sensors such as strain gauges may be used on the bonded portion between the trapezoidal-based CFRP strip and the concrete prism 110 to record strains for further analysis.

Figure 16:
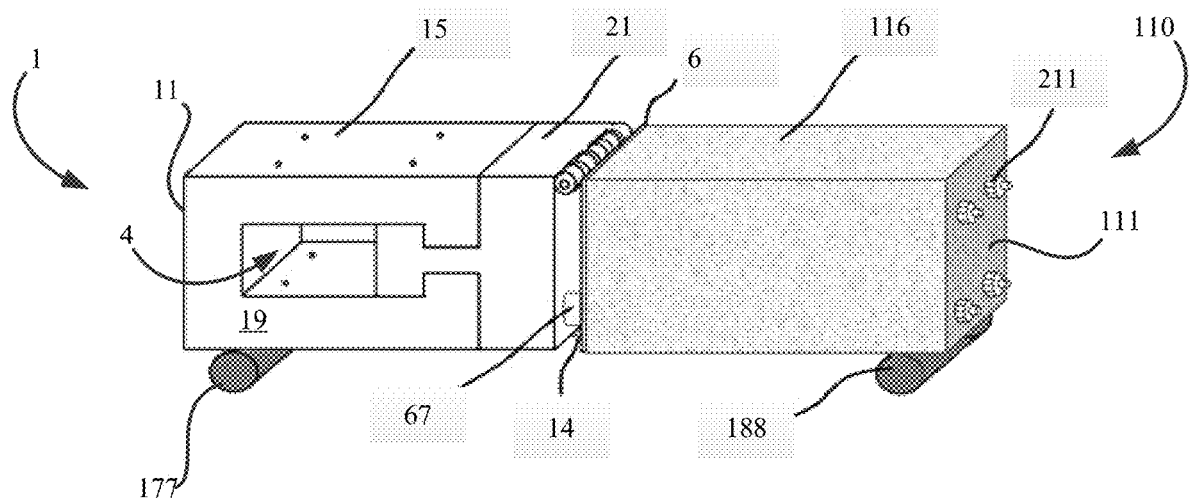
FIG. 16 is a perspective view and a side view illustrating the test apparatus of the present disclosure being used for beam-bending tests.
Figure 16:
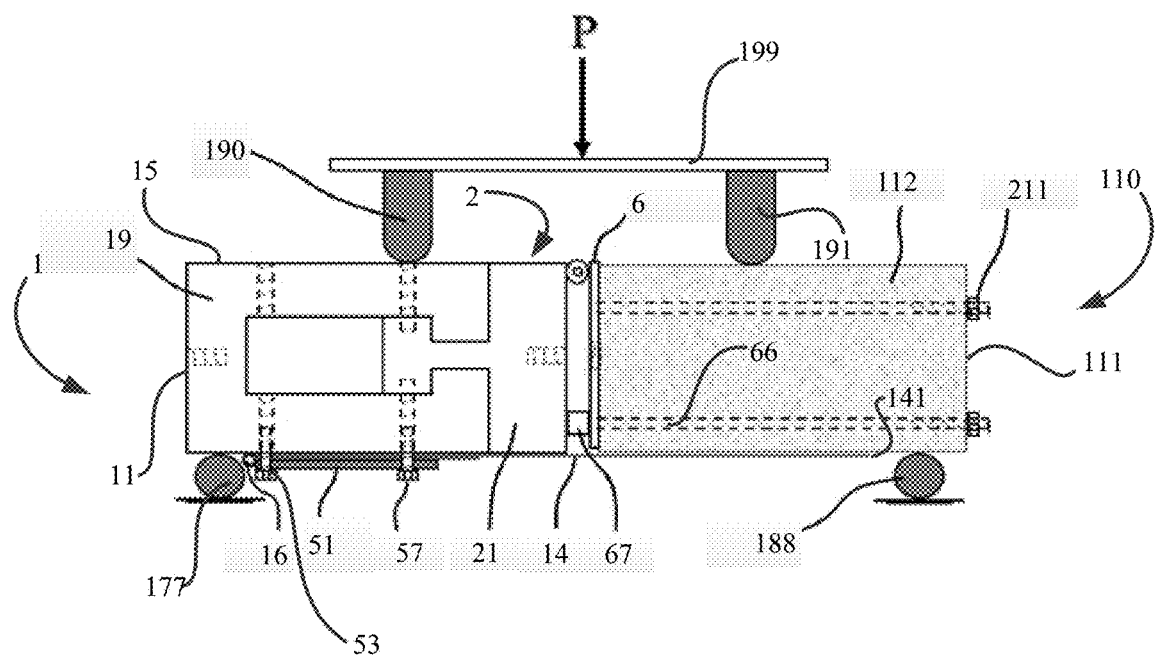
Figure 17:
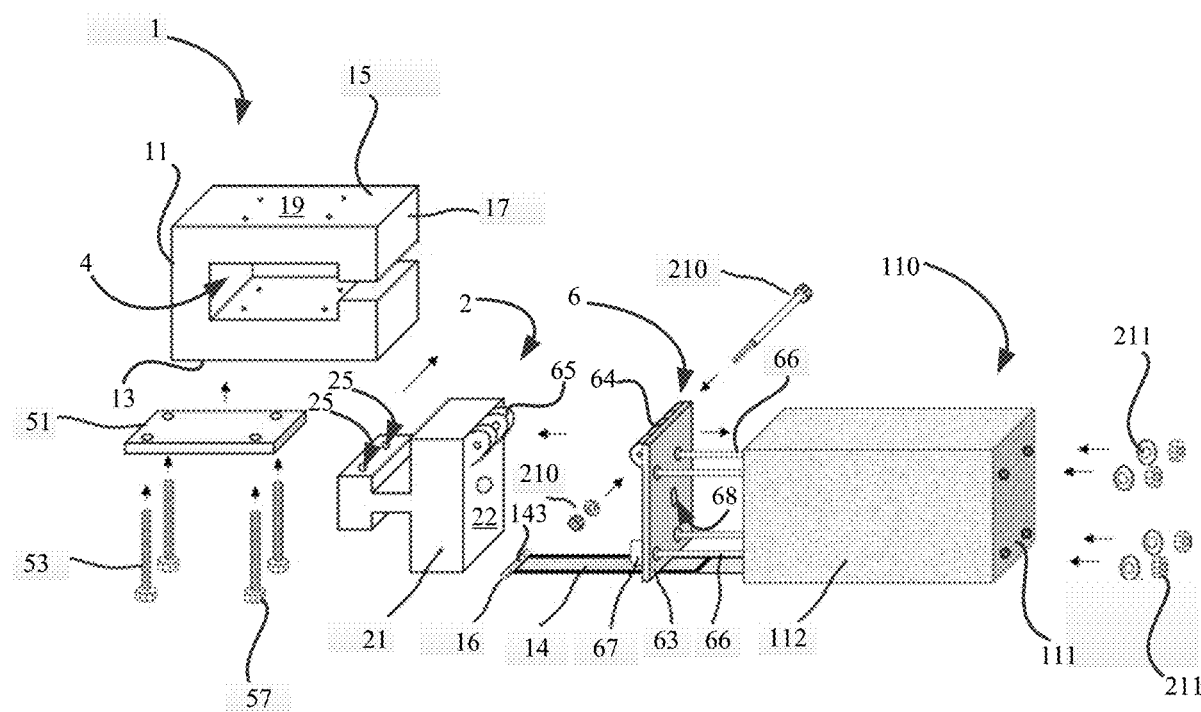
FIG. 17 is a perspective exploded view illustrating the test apparatus of the present disclosure being used for beam-bending tests.

As seen in FIG. 16 and FIG. 17, in order to use the test apparatus of the present disclosure for beam-bending tests, a concrete prism 110 with a planar CFRP strip 14 is provided. As an initial step of performing the beam-bending test, the secondary structural block 2 is positioned into the receiving slot 4. The connecting plate 6 is pivoted towards the bottom surface 22 of the secondary structural block 2 such that the pair of optional stoppers 67 is pressed in between the bottom surface 22 of the secondary structural block 2 and the first surface 61 of the connecting plate 6. The plurality of rods 66 extending from the second surface 63 penetrate into a second surface 113 of the concrete prism 110 and traverses through a structural body of the concrete prism 110. The plurality of rods 66 is secured within the structural body of the concrete prism 110 through a fastening mechanism that can be, but is not limited to, a bolt/nut/washer system. A first end 141 of the planar CFRP strip 14 is adhered to a first lateral surface 115 of the concrete prism 110. A second end of the planar CFRP strip 14 is, first, folded over an anchor rod 16 and the overlapping portion of the planar CFRP strip 14 is glued together. Next, an overlapping end 143 resulting from the overlapping portion is attached to a first lateral surface 13 of the primary structural block 1. An attachment plate 51 is used to secure the planar CFRP strip 14 against the first lateral surface 13. In doing so, the attachment plate 51 is mounted onto the first lateral surface 13 of the primary structural block 1 using the attachment mechanism 5. Thus, the planar CFRP strip 14 is positioned in between the attachment plate 51 and the first lateral surface 13 of the primary structural block 1. In particular, the attachment plate 51 will be positioned adjacent the second end 143 of the planar CFRP strip 14 and the anchor rod 16. Consequently, the anchor rod 16 over which a second end of the CFRP strip is folded acts as a further stopper by wedging against the attachment plate 51 of the attachment mechanism 5.

As a next step of the beam-bending test, the primary structural block 1 is rested against a first support 177, wherein the first support 177 is positioned against the first lateral surface 13 of the primary structural block 1. Moreover, the first support 177 is positioned in between a top surface 11 of the primary structural block 1 and the anchor rod 16 used at the second end 143 of the planar CFRP strip 14. Next, the concrete prism 110 is rested against a second support 188, wherein the second support 188 is positioned against the first lateral surface 115 of the concrete prism 110. Moreover, the second support 188 is positioned in between a first surface 111 of the concrete prism 110 and the first end 141 of the planar CFRP strip 14. When appropriately positioned, the beam-bending test is executed by applying a load through a load beam 199. A first load point 190 of the load beam 199 is applied onto a second lateral surface 15 of the primary structural block 1. On the other hand, a second load point 191 is applied onto a second lateral surface 116 of the concrete prism 110. A set of beam-bending characteristics of the planar CFRP strip 14 is analyzed according to the load applied through the first load point 190 and the second load point 191. Other than the loading mechanism, some additional means of data acquisition sensors such as strain gauges or linear variable transducers may be used on the bonded portion between the planar CFRP strip and the concrete prism 110 to record strains and displacements for further analysis.

Figure 18:
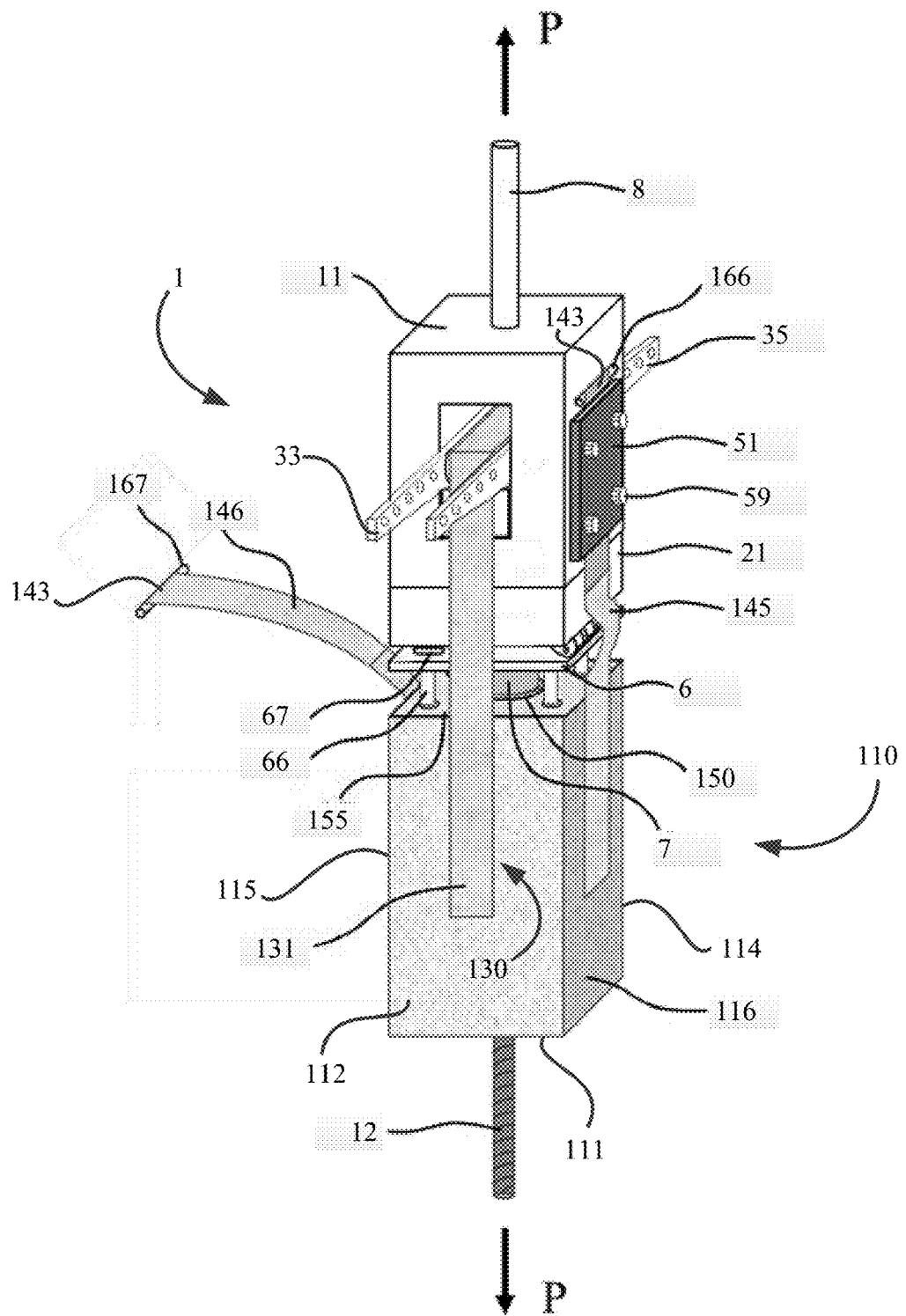
FIG. 18 is a perspective view illustrating a setup that can be implemented with the test apparatus of the present disclosure for sequential testing of double-shearing, single-shearing, shearing-and-peeling, tension pull-off, and beam-bending.

As seen in FIG. 18, the test apparatus described in the present disclosure can also be used to sequentially perform the double-shear test, the single-shear test, the tension pull-off test, and the beam-bending test. To do so, a concrete prism 110 with a first planar CFRP strip 145, a second planar CFRP strip 146, a U-shaped CFRP strip 130, and a CFRP sheet 155 is provided. As in the tests described earlier, the loading rebar 12 centrally penetrates into the first surface 111 of the concrete prism 110. With the secondary structural block 2 positioned into the receiving slot 4, and the plurality of rods 66 extending from the connecting plate 6 positioned through the second surface 113 of the concrete prism 110, the connecting plate 6 is pivoted towards the bottom surface 22 of the secondary structural block 2.

To perform the single-shear test, a first end 141 of the first planar CFRP strip 145 is adhered to the second lateral surface 116 of the concrete prism 110 and a second end of the first planar CFRP strip 145 is attached to a second lateral surface 15 of the primary structural block 1. Similar to the single-shear test described previously, the first planar CFRP strip 145 is held against the second lateral surface 51 using the attachment plate 15 and the attachment mechanism 5. The second end is preferably folded over a first anchor rod 166 and the overlapping portion is glued prior to fixing the overlapping end 143 to the second lateral surface 15 with attachment mechanism 5.

To perform the beam-bending test, a first end 141 of the second planar CFRP strip 146 is adhered to a first lateral surface 115 of the concrete prism 110 and an overlapping end 143 of the second planar CFRP strip 146 is left detached from the first lateral surface 13 of the primary structural block 1 during double-shear, single-shear, and tension pull-off tests.

To perform the double-shear test, the U-shaped CFRP strip 130 is positioned similar to the setup discussed in the double-shear test that minimizes eccentricity. In particular, a first end 131 is attached to the front surface 112. A second end 135 is attached onto the rear surface 114 such that a base portion 133 is positioned adjacent the top end 41 of the receiving slot 4. The adjustable hanger 3 holds the base portion 133 against the top end 41.

To perform the tension pull-off test, the CFRP sheet 155 is attached to the second surface 113 of the concrete prism 110. Moreover, the tension pull-off disk 7 is adhered to the CFRP sheet 155 while being concentrically aligned with the circular channel 150.

As a first test, the tension pull-off test is performed with the test apparatus described in the present disclosure. In doing so, a first load is applied along the loading rebar 12 and a second load is applied along the threaded gripping rod 8 which traverses into the top surface 11 of the primary structural block 1. Similar to the previous instances, the first load is substantially equal in magnitude but is opposite in direction to the second load. In order to perform the tension pull-off test without hindering the U-shaped CFRP strip 130 or the first planar CFRP strip 145, the U-shaped CFRP strip 130 and the first planar CFRP strip 145 are attached between the primary structural block 1 and the concrete prism 110 with suitable slack lengths.

As a second test, the double-shear test is performed with the test apparatus described in the present disclosure. As described earlier, the primary distance 103 and the secondary distance 104 are minimal when the double-shear test is performed. However, when the primary distance 103 and the secondary distance 104 are greater than the minimal value, mixed-mode testing can be performed with the test apparatus of the present disclosure.

As a third test, the single-shear test is performed with the test apparatus described in the present disclosure. To do so, the shearing in the first planar CFRP strip 145 is analyzed.

As a fourth test, the beam-bending test is performed after the first test, the second test, and the third test are completed. However, the tension pull-off disk 7 needs to be removed after conducting the previous three tests, and the already tested U-shaped CFRP strip 130 from the double-shear test and the first planar CFRP strip 145 from the single-shear test need to be cut and removed. Then the attachment plate 51 needs to be removed from the second lateral surface 15 and used to secure the second planar CFRP strip 146 in a similar manner described previously when conducting the beam-bending test. In order to perform the beam-bonding test, the second end of the second planar CFRP strip 146 is attached to the first lateral surface 13 of the primary structural block 1 with an attachment plate 51. The first end 141 of the planar CFRP strip 14 is adhered to a first lateral surface 115 of the concrete prism 110. The attachment mechanism 5 is preferably used to attach the attachment plate 51 against the first lateral surface 13. Moreover, a second anchor rod 167 is preferably used when attaching the overlapping end 143 to the first lateral surface 13. More specifically, the second end of the planar CFRP strip 14 is, first, folded over a second anchor rod 167 and the overlapping portion of the second planar CFRP strip 146 is glued together. Next, an overlapping end 143 resulting from the overlapping portion is attached to a first lateral surface 13 of the primary structural block 1. The attachment plate 51, removed from the second lateral surface 15 is used to secure the planar CFRP strip 14 against the first lateral surface 13. Next, as described in the beam-bending test, a load is applied through a first load point 190 and a second load point 191 of a load beam 199.

Terminology. Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A debonding test apparatus, comprising:
   a primary structural block having a receiving slot formed therein;
   a secondary structural block;
   an adjustable hanger;
   an attachment mechanism;
   the primary structural block comprises a top surface, a first lateral surface, a second lateral surface, a bottom surface, and a structural body;
   the structural body extending from the top surface to the bottom surface in between the first lateral surface and the second lateral surface;
   the receiving slot traversing through the structural body of the primary structural block in between the first lateral surface and the second lateral surface adjacent the bottom surface of the primary structural block;
   the adjustable hanger being slidably positioned into the receiving slot adjacent a top end of the receiving slot;
   the secondary structural block being slidably positioned into the receiving slot adjacent a bottom end of the receiving slot, wherein the adjustable hanger is positioned atop the secondary structural block; and
   the primary structural block, the secondary structural block, and the adjustable hanger being detachably attached to each other through the attachment mechanism.

2. The debonding test apparatus as of claim 1 further comprising:
   a connecting plate having a circular opening;
   a first plurality of hinges;
   a second plurality of hinges;
   a plurality of rods;
   the first plurality of hinges being laterally positioned along a length of a first surface of the connecting plate;
   the second plurality of hinges being positioned along a length of a bottom surface of the secondary structural block;
   the plurality of rods being perpendicularly connected to a second surface of the connecting plate, wherein a distance between the first surface and the second surface determines a thickness of the connecting plate; and
   the first plurality of hinges and the second plurality of hinges being engageable with one another with a first set of fastening nuts/washers such that the connecting plate is connected to the bottom surface of the secondary structural block.

3. The debonding test apparatus as of claim 2 further comprising:
   a pair of optional stoppers; and
   the pair optional stoppers extending from the first surface opposite the first plurality of hinges.

4. The method of using the debonding test apparatus as of claim 2 comprising the steps of:
   wherein a double-shear test is performed on a concrete prism with a U-shaped CFRP strip,
   wherein a first end of the U-shaped CFRP strip is attached onto a front surface of the concrete prism, wherein a second end of the U-shaped CFRP strip is attached onto a rear surface of the concrete prism such that a base portion of the U-shaped CFRP strip is offset from and parallel to a second surface of the concrete prism;
wherein a loading rebar centrally penetrates into a first surface of the concrete prism;
positioning the base portion adjacent a top end of the receiving slot, wherein the first end and the second end of the U-shaped CFRP strip are oriented towards the bottom end of the receiving slot;
positioning the adjustable hanger into the receiving slot such that the adjustable hanger is adjacent the base portion and opposite the top end in a flipped configuration;
sliding the secondary structural block into the receiving slot such that the adjustable hanger is positioned in between the base portion and the secondary structural block;
positioning the plurality of rods through a second surface of the concrete prism;
threadably engaging a threaded gripping rod into a top-receiving channel traversing into a top surface of the primary structural block;
attaching the connecting plate to the bottom surface of the secondary structural block using the first plurality of hinges, the second plurality of hinges, and the first set of fastening nuts/washers, and pressing a pair of optional stoppers against the bottom surface of the secondary structural block, wherein a threaded protrusion connected to a tension pull-off disk is positioned through the circular opening and into a bottom-receiving channel in order to hold the connecting plate fixed to the secondary structural block;
simultaneously applying a first load along the loading rebar and a second load along the threaded gripping rod, wherein the first load and the second load are substantially equal in magnitude and opposite in direction;
measuring a shear load for the first load and the second load, wherein the shear load is when shearing occurs in the U-shaped CFRP strip;
recording strain and loaded end displacements at a bonded portion using a set of data acquisition sensors, wherein the bonded portion is between the U-shaped CFRP strip and the concrete prism.

5. The method of using the debonding test apparatus as of claim 2 comprising the steps of:
wherein a single-shear test is performed on a concrete prism with a planar CFRP strip,
wherein a first end of the planar CFRP strip is adhered to a second lateral surface of the concrete prism and a second end of the planar CFRP strip is folded over an anchor rod and an overlapping end is attached to a second lateral surface of the primary structural block;
wherein a loading rebar centrally penetrates into a first surface of the concrete prism;
positioning the secondary structural block into the receiving slot;
attaching the connecting plate to the bottom surface of the secondary structural block using the first plurality of hinges, the second plurality of hinges, and the first set of fastening nuts/washers, and pressing a pair of optional stoppers against the bottom surface of the secondary structural block, wherein a threaded protrusion connected to a tension pull-off disk is positioned through the circular opening and into a bottom-receiving channel in order to hold the connecting plate fixed to the secondary structural block;
positioning the plurality of rods through a second surface of the concrete prism;
mounting an attachment plate onto the second lateral surface of the primary structural block using the attachment mechanism, wherein a body portion of the planar CFRP strip is positioned in between the attachment plate and the second lateral surface of the primary structural block, wherein the attachment plate is positioned adjacent the second end of the CFRP strip;
threadably engaging a threaded gripping rod into a top-receiving channel traversing into a top surface of the primary structural block;
simultaneously applying a first load along the loading rebar and a second load along the threaded gripping rod, wherein the first load and the second load are substantially equal in magnitude and opposite in direction;
measuring a shear load for the first load and the second load, wherein the shear load is when shearing occurs in the planar CFRP strip;
recording strain and loaded end displacements at a bonded portion using a set of data acquisition sensors, wherein the bonded portion is between the planar CFRP strip and the concrete prism.

6. The method of using the debonding test apparatus as of claim 2 comprising the steps of:
wherein a beam-bending test is performed on a concrete prism with a planar CFRP strip,
wherein a first end of the planar CFRP strip is adhered to a first lateral surface of the concrete prism and a second end of the planar CFRP strip folded over an anchor rod such that an overlapping end is connected to a first lateral surface of the primary structural block using the attachment mechanism;
positioning the secondary structural block into the receiving slot;
pivoting the connecting plate towards the bottom surface of the secondary structural block and pressing a pair of optional stoppers against the bottom surface of the secondary structural block;
penetrating the plurality of rods into a second surface and through a structural body of the concrete prism, wherein the plurality of rods is secured using a second set of fastening nuts/washers;
mounting an attachment plate against the first lateral surface of the primary structural block using the attachment mechanism, wherein the planar CFRP strip is positioned in between the attachment plate and the first lateral surface of the primary structural block, wherein the attachment plate is positioned adjacent the overlapping end of the planar CFRP strip;
resting the primary structural block against a first-support, wherein the first support is positioned against the first lateral surface of the primary structural block in between a top surface of the primary structural block and the anchor rod;
resting the concrete prism against a second support, wherein the second support is positioned against the first lateral surface of the concrete prism in between a first surface of the concrete prism and the first end of the planar CFRP strip;
applying a load through a load beam, wherein a first load point of the load beam is applied onto a second lateral surface of the primary structural block and a second load point of the load beam is applied onto a second lateral surface of the concrete prism;

analyzing a set of beam-bending characteristics according to the first load and the second load; and recording strain and loaded end displacements at a bonded portion using a set of data acquisition sensors, wherein the bonded portion is between the planar CFRP strip and the concrete prism.

7. The debonding test apparatus as of claim 1 further comprising:

a tension pull-off disk;

a threaded protrusion;

a bottom-receiving channel;

the bottom-receiving channel perpendicularly penetrating into a bottom surface of the secondary structural block;

the threaded protrusion being perpendicularly connected to a structural body of the tension pull-off disk; and the threaded protrusion being threadably engaged with a plurality of threads of the bottom-receiving channel, wherein the plurality of threads is internally distributed along the bottom-receiving channel.

8. The method of using the debonding test apparatus as of claim 7 comprising the steps of:

wherein a tension pull-off test is performed on a concrete prism with a CFRP sheet, wherein the CFRP sheet is adhered to a second surface of the concrete prism, wherein a circular channel centrally traverses into the second surface of the concrete prism through the CFRP sheet, wherein a loading rebar centrally penetrates into a first surface of the concrete prism;

pressing and adhering the tension pull-off disk onto the CFRP sheet opposite the threaded protrusion, wherein the tension-pull off disk is concentrically aligned with the circular channel;

threadably engaging a threaded gripping rod into the top-receiving channel traversing into a top surface of the primary structural block;

simultaneously applying a first load along the loading rebar and a second load along the threaded gripping rod, wherein the first load and the second load are substantially equal in value and opposite in direction; and measuring a pull-off load for the first load and the second load, wherein pull-off load corresponds to debonding between the CFRP sheet and the concrete prism.

9. The debonding test apparatus as of claim 1 further comprising:

a threaded gripping rod;

the top surface of the primary structural block having formed therein a top-receiving channel that traverses the top surface of the primary structural block; and the threaded gripping rod being threadably engaged with a plurality of threads of the top-receiving channel, wherein the plurality of threads is internally distributed along the top-receiving channel.

10. The debonding test apparatus as of claim 1, wherein the attachment mechanism comprises a first pair of hanger-fastening bolts, a second pair of hanger-fastening bolts, a first pair of block-fastening bolts, and a second pair of block-fastening bolts;

the first pair of hanger-fastening bolts traversing through the first lateral surface and pressing into and against a first pair of hanger bolt-receiving slots that laterally traverse into a central block of the adjustable hanger;

the first pair of block-fastening bolts traversing through the first lateral surface and pressing into and against a first pair of block bolt-receiving slots that laterally traverse into a structural body of the secondary structural block;

the second pair of hanger-fastening bolts traversing through the second lateral surface and pressing into and against a second pair of hanger bolt-receiving slots that laterally traverse into the central block of the adjustable hanger opposite the first pair of hanger bolt-receiving slots; and the second pair of block-fastening bolts traversing through the second lateral surface and pressing into and against a second pair of block bolt-receiving slots that laterally traverse into the structural body of the secondary structural block opposite the first pair of block-fastening bolts.

11. The debonding test apparatus as of claim 1 further comprising:

the adjustable hanger comprises a central block, a first arm portion, a second arm portion, and a plurality of receiving slots formed in the hanger;

the central block being positioned in between the first arm portion and the second arm portion; and the plurality of receiving slots perpendicularly traversing through the first arm portion and the second arm portion adjacent the central block.

12. The debonding test apparatus as of claim 11 further comprising:

a pair of solid cylinders;

a pair of hollow cylinders;

a first hollow cylinder from the pair of hollow cylinders being positioned in between the first arm portion and the second arm portion;

the first hollow cylinder being concentrically aligned with the first selected receiving slot;

a first solid cylinder from the pair of solid cylinders being concentrically aligned with the first selected receiving slot; and the first solid cylinder being slidably positioned through the first selected receiving slot traversing the first arm portion, the first hollow cylinder, and the first selected receiving slot traversing the second arm portion.

13. The debonding test apparatus as of claim 12 further comprising:

a first-fastening mechanism; and the first solid cylinder being secured within the first hollow cylinder through the first-fastening mechanism.

14. The debonding test apparatus as of claim 11 further comprising:

wherein the second selected receiving slot is positioned opposite a first selected receiving slot selected from the plurality of receiving slots across the central block;

a pair of solid cylinders;

a pair of hollow cylinders;

a second hollow cylinder from the pair of hollow cylinders being positioned in between the first arm portion and the second arm portion;

the second hollow cylinder being concentrically aligned with the second selected receiving slot;

a second solid cylinder from the pair of solid cylinders being concentrically aligned with the second selected receiving slot; and the second solid cylinder being slidably positioned through the second selected receiving slot traversing first arm portion, the second hollow cylinder, and the second selected receiving slot traversing the second arm portion.

15. The debonding test apparatus as of claim 14 further comprising:
a second-fastening mechanism; and
the second solid cylinder being secured within the second hollow cylinder through the second-fastening mechanism.

16. The debonding test apparatus as of claim 11 further comprising:
wherein a primary distance is measured from a center of the central block to a first selected receiving slot from the plurality of receiving slots;
wherein a secondary distance is measured from a center of the central block to a second selected receiving slot from the plurality of receiving slots; and
wherein the primary distance is equivalent to the secondary distance.

17. The method of using the debonding test apparatus as of claim 11 comprising the steps of:
wherein a mixed-mode test is performed on a concrete prism with a trapezoidal-based CFRP strip,
wherein a loading rebar centrally penetrates into a first surface of the concrete prism;
wherein a long base of the trapezoidal-based CFRP strip is offset and is positioned in parallel to a second surface of the concrete prism,
wherein a first leg of the trapezoidal-based CFRP strip makes a first peeling angle with the front surface of the concrete prism;
wherein a second leg of the trapezoidal-based CFRP strip makes a second peeling angle with the rear surface of the concrete prism,
positioning the adjustable hanger into the receiving slot adjacent the top end in an upright configuration;
positioning the long base in between and in parallel the first arm portion and the second arm portion;
positioning a first hollow cylinder in between the first arm portion and the second arm portion, wherein the first hollow cylinder is selected from a pair of hollow cylinders and intersects a base angle between the first leg and the long base;
positioning a second hollow cylinder in between the first arm portion and the second arm portion, wherein the second hollow cylinder is selected from a pair of hollow cylinders and intersect a base angle between the second leg and the long base;
inserting a first solid cylinder through a first selected receiving slot of the first arm portion, the first hollow cylinder, and the first selected receiving slot of the second arm portion, wherein the first selected receiving slot is selected from the plurality of receiving slots;
inserting a second solid cylinder through a second selected receiving slot of the first arm portion, the second hollow cylinder, and the second selected receiving slot of the second arm portion, wherein the second selected receiving slot is selected from the plurality of receiving slots;
sliding the secondary structural block into the receiving slot such that the long base is positioned in between the adjustable hanger and the secondary structural block;
threadably engaging a threaded gripping rod into a bottom-receiving channel traversing into a bottom surface of the secondary structural block;
simultaneously applying a first load along the loading rebar and a second load along the threaded gripping rod, wherein the first load and the second load are substantially equal in value and opposite in direction;
measuring the first peeling angle and the second peeling angle according to the first load and the second load;
recording strain and loaded end displacements at a bonded portion using a set of data acquisition sensors, wherein the bonded portion is between the trapezoidal-based CFRP strip and the concrete prism.

18. A method of using the debonding test apparatus as of claim 1 comprising the steps of:
wherein a double-shear test is performed on a concrete prism with a U-shaped carbon fibre reinforced polymer (CFRP) strip,
wherein a first end of the U-shaped CFRP strip is attached onto a front surface of the concrete prism,
wherein a second end of the U-shaped CFRP strip is attached onto a rear surface of the concrete prism such that a base portion of the U-shaped CFRP strip is offset from and positioned in parallel to a second surface of the concrete prism;
wherein a loading rebar centrally penetrates into a first surface of the concrete prism;
positioning the adjustable hanger into the receiving slot adjacent the top end in an upright configuration;
positioning the base portion into the receiving slot through the bottom surface of the primary structural block such that the base portion is wrapped around a central block of the adjustable hanger;
sliding the secondary structural block into the receiving slot such that the base portion is positioned in between the adjustable hanger and the secondary structural block;
threadably engaging a threaded gripping rod into a bottom-receiving channel traversing into a bottom surface of the secondary structural block;
simultaneously applying a first load along the loading rebar and a second load along the threaded gripping rod, wherein the first load and the second load are substantially equal in magnitude and opposite in direction;
measuring a shear load for the first load and the second load, wherein the shear load is when shearing occurs in the U-shaped CFRP strip; and
recording strain and loaded end displacements at a bonded portion using a set of data acquisition sensors, wherein the bonded portion is between the U-shaped CFRP strip and the concrete prism.

19. The method of using the debonding test apparatus as of claim 1 comprising the steps of:
wherein a sequential multi-test is performed on a concrete prism with a first planar CFRP strip, a second planar CFRP strip, a U-shaped CFRP strip, and a CFRP sheet,
wherein a loading rebar centrally penetrates into a first surface of the concrete prism,
wherein a threaded gripping rod is threadably engaged into the top-receiving channel traversing into a top surface of the primary structural block,
wherein a first end of the U-shaped CFRP strip is attached onto a front surface of the concrete prism,
wherein a second end of the U-shaped CFRP strip is attached onto a rear surface of the concrete prism such that a base portion of the U-shaped CFRP strip is offset from and parallel to a second surface of the concrete prism,
wherein a first end of the first planar CFRP strip is adhered to a second lateral surface of the concrete prism and a second end of the planar CFRP strip is folded over a first anchor rod and an overlapping end is attached to a second lateral surface of the primary structural block, wherein a first end of the second planar CFRP strip is adhered to a first lateral surface of the concrete prism, wherein the CFRP sheet is adhered to a second surface of the concrete prism;

simultaneously applying a first load along the loading rebar and a second load along the threaded gripping rod, wherein the first load and the second load are substantially equal in value and opposite in direction;

measuring a pull-off load for the first load and the second load, wherein the pull-off load corresponds to debonding between the CFRP sheet and the concrete prism;

simultaneously applying a first load along the loading rebar and a second load along the threaded gripping rod, wherein the first load and the second load are substantially equal in magnitude and opposite in direction;

measuring a shear load for the first load and the second load, wherein the shear load is when shearing occurs in the U-shaped CFRP strip;

recording strain and loaded end displacements at a bonded portion using a set of data acquisition sensors, wherein the bonded portion is between the U-shaped CFRP strip and the concrete prism;

simultaneously applying a first load along the loading rebar and a second load along the threaded gripping rod, wherein the first load and the second load are substantially equal in magnitude and opposite in direction;

measuring a shear load for the first load and the second load, wherein the shear load is when shearing occurs in the first planar CFRP strip;

recording strain and loaded end displacements at a bonded portion using a set of data acquisition sensors, wherein the bonded portion is between the first planar CFRP strip and the concrete prism;

removing the tension pull-off disk, the U-shaped CFRP strip, and the first planar CFRP strip;

folding a second end of the planar CFRP strip over a second anchor rod and attaching an overlapping end to a first lateral surface of the primary structural block;

applying a load through a load beam, wherein a first load point of the load beam is applied onto a second lateral surface of the primary structural block and a second load point of the load beam is applied onto a second lateral surface of the concrete prism;

analyzing a set of beam-bending characteristics according to the first load and the second load; and recording strain and loaded end displacements at a bonded portion using a set of data acquisition sensors, wherein the bonded portion is between the second planar CFRP strip and the concrete prism.

* * * * *